US005744320A

United States Patent [19]
Sherf et al.

[11] Patent Number: 5,744,320
[45] Date of Patent: Apr. 28, 1998

[54] QUENCHING REAGENTS AND ASSAYS FOR ENZYME-MEDIATED LUMINESCENCE

[75] Inventors: Bruce A. Sherf, Waunakee; Keith V. Wood, Madison; Elaine T. Schenborn, Middleton, all of Wis.

[73] Assignee: Promega Corporation, Madison, Wis.

[21] Appl. No.: 472,546

[22] Filed: Jun. 7, 1995

[51] Int. Cl.$^6$ .............................. C12Q 1/66; C12Q 1/00; C12Q 1/37; C09K 11/06
[52] U.S. Cl. ......................... 435/8; 435/4; 435/975; 435/963; 435/23; 252/301.16; 252/646; 356/4.01
[58] Field of Search ............... 435/8, 4, 975, 435/963, 23; 252/301.16, 646, 4.01; 356/4.01

[56] References Cited

U.S. PATENT DOCUMENTS

| | | | |
|---|---|---|---|
| 4,235,961 | 11/1980 | Lundin | 435/8 |
| 4,390,274 | 6/1983 | Berthold et al. | 435/8 |

FOREIGN PATENT DOCUMENTS

| | | |
|---|---|---|
| 0 054 676 | 6/1982 | European Pat. Off. |
| 0 247 796 | 12/1987 | European Pat. Off. |
| 0 342 024 | 11/1989 | European Pat. Off. |
| 0610937 | 10/1994 | European Pat. Off. |
| WO 91/18116 | 11/1991 | WIPO |
| WO 92/04468 | 3/1992 | WIPO |

OTHER PUBLICATIONS

Blaise, C., et al. (1994) BioTechniques: 16, 932–937, month not available.
Bronstein, et al. (1991) Chemiluminescence and Bioluminescence: Current Status. (eds. PE Stanley and L.J. Kricka) John Wiley & Sons, Inc. pp. 169–181, month not available.
Bronstein, I., et al. (1994) Anal–Biochem.: 219, 73–82. month not available.
Denburg, et al. (1969) Archives of Biochemistry and Biophysics: 134, 381–394, month not available.
Denburg, J.L., and McElroy, W.D. (1970) Archives of Biochemistry and Biophysics: 141, 668–675, month not available.
Flanagan, W. M. et al. (1991) J. Virology: 65, 769–786, month not available.
Jain, V. K. and Magrath, I. T. (1992) BioTechniques: 12, 681–683, month not available.
Kobatake, E. et al. (1993) Analytical Biochemistry: 208, 300–305, month not available.
Leckie, F. et al. (1994) BioTechniques: 17, 52–57, month not available.
Lee, et al. (1970) Archives of Biochemistry and Biophysics: 141, 38–52, month not available.
Mathews, J. C. et al. (1977) Biochemistry: 16, 85–91, month not available.
Schaap, et. al. (1989) Clinical Chemistry: 35, 1863–1864, month not available.
Schram, (1991) Bioluminescence and Chemiluminescence: Current Status. (eds. P.E. Stanley and L.J. Kricka) John Wiley & Sons, Inc., pp. 407–412, month not available.
Thompson, J. F., et al. (1991) Gene: 103, 171–177, month not available.
Thorp, et al. (1986) Methods in Enzymology: 133, 331–353, month not available.
Ward (1985) Chemi–and Bioluminescence (ed. John Burr) Marcel Dekker, Inc., New York, pp. 321–358, month not available.
Wood (1995) Curr. Op. Biotech.: 6, 50–58, month not available.
Wood, K. (1991) in Bioluminescence & Chemiluminescence: Current Status. (eds. Stanley, P. E., and Kricka, J.) John Wiley & Sons, Chichester. pp. 543–546, month not available.

*Primary Examiner*—Louise Leary
*Attorney, Agent, or Firm*—DeWitt Ross & Stevens SC

[57] ABSTRACT

The present invention relates to single and dual-reporter luminescence assays utilizing general and specific reagents to quench enzyme-mediated reactions. In one embodiment of the invention, a reagent is added to the assay which non-specifically quenches enzyme-mediated luminescent reactions. In another embodiment of the invention, a reagent is added to the assay which simultaneously quenches one enzyme-mediated luminescent reaction while activating another distinct enzyme-mediated luminescent reaction. An assay kit containing specific quench reagents, and the reagents themselves are also disclosed.

60 Claims, 6 Drawing Sheets

QUENCHING REAGENTS AND ASSAYS FOR ENZYME-MEDIATED LUMINESCENCE

FIELD OF THE INVENTION

The present invention relates to enzyme-mediated single and dual-reporter luminescence assays, and reagents which quench the luminescence reactions. Specifically, the present invention is directed to luminescence assays utilizing at least one enzyme, and one: or more luminescence quench reagents.

CITED REFERENCES

Full bibliographic citations to the references cited in this application can be found in the section preceding the claims.

DESCRIPTION OF THE PRIOR ART

Luminescence is produced in certain organisms as a result of luciferase-mediated oxidation reactions. Currently, luciferase genes from a wide variety of vastly different species, particularly the luciferase genes of Photinus pyralis (the common firefly of North America), Pyrophorus plagiophthalamus (the Jamaican click beetle), Renilla reniformis (the sea pansy), and several bacteria (e.g., Xenorhabdus luminescens and Vibrio spp), are extremely popular luminescence reporter genes. Reference is made to Bronstein, et al. (1994) for a review of luminescence reporter gene assays. Firefly luciferase is also a popular reportel for ATP concentrations, and in that role is widely used to detect biomass. Various other reporter applications of luciferases have been described in the scientific literature. Luminescence may be produced by other enzymes when mixed with certain synthetic substrates; such as alkaline phosphatase mixed with adamantyl dioxctanes, or horseradish peroxidase mixed with luminol.

Luciferase genes are widely used as genetic reporters due to the non-radioactive nature, sensitivity, and extreme linear range of luminescence assays. For instance, as few as $10^{-20}$ moles of the firefly luciferase can be detected. Consequently, luciferase assays of gene activity are used in virtually every experimental biological system, including both prokaryotic and eukaryotic cell cultures, transgenic plants and animals, and cell-free expression systems. Similarly, luciferase assays of ATP are highly sensitive, enabling detection to below $10^{-16}$ moles.

Luciferases generate light via the oxidation of enzyme-specific substrates, called luciferins. For firefly luciferase and all other beetle luciferases, this is done in the presence of magnesium ions, oxygen, and ATP. For anthozoan luciferases, including Renilla luciferase, only oxygen is required along with the luciferin. Generally, in iuminescence assays of genetic activity, reaction substrates and other luminescence-activating reagents are introduced into a biological system suspected of expressing a reporter enzyme. Resultant luminescence, if any, is then measured using a luminometer or any suitable radiant energy-measuring device. The assay is very rapid and sensitive, and provides gene expression data quickly and easily, without the need for radioactive reagents. Reporter assays other than for genetic activity are performed analogously.

The conventional assay of genetic activity using firefly luciferase has been further improved by including coenzyme A (CoA) in the assay reagent to yield greater enzyme turnover and thus greater luminescence intensity. (Promega Luciferase Assay Reagent, Cat. No. E1500, Promega Corporation, Madison, Wis.; see U.S. Pat. No. 5,283,179, issued Feb. 1, 1994.) Using this reagent, luciferase activity can be readily measured in luminometers or scintillation counters. The luciferase reaction, modified by the addition of CoA to produce persistent light emission, provides an extremely sensitive and rapid assay for quantifying luciferase expression in genetically altered cells or tissues.

A major drawback, however, to the use of luminescence assays in high-throughput applications is their incompatibility with standard laboratory equipment. For instance, it is not possible to quantify luminescence reactions contained in clear multi-well plates with precision or accuracy because of the internal refraction of light through the optically clear plate. FIG. 1 demonstrates that, when using conventional 96-well clear polystyrene microtiler plates, the luminescence signal generated in one well is refracted through the plastic over relatively long distances. Hence, the light refracted from one luminous sample can interfere with the subsequent measurement of signal from luminescent samples in successive wells. FIG. 2 shows the cumulative nature of refracted light emanating from multiple luminous samples within a single clear plastic plate. While the luminescent signal in the first sample well can be measured accurately, sequential activation of luminescent reactions in following wells leads to increasingly inaccurate measurements due to the cumulative emission of photons refracted through the plastic from all previous samples. This problem of refracted light, or "refractive cross-talk" is further exacerbated when brightly illuminated wells are situated adjacent to negative control wells in which no luminescence is generated, or when brightly lit wells are situated near relatively dim wells. This makes determining the absolute and baseline luminescence in a clear multi-well plate difficult, if not impossible.

Multi-well plates made from opaque plastics such as white and black polyethylene are commercially available (e.g., DynaTech Laboratories, Chantilly, Va; Labsystems, Helsinki, Finland; NUNC, Roskilde, Demnark), and are now being adopted to prevent refractive cross-talk between samples in applications involving high-throughput luminometric analysis (Blaise, C., et al., 1994). However, while the reflectivity of white plastic yields greater luminescence sensitivity than clear plates, photons are readily scattered from the walls of adjacent wells, again introducing cross-talk interference between wells. Here, the cross-talk is referred to as "reflective cross-talk." In the same manner as refractive cross-talk, reflective cross-talk is particularly evident when assaying dim wells (such as negative controls not containing luciferase) that are adjacent to bright wells. Black 96-well plates, originally intended for fluorescent applications, are not ideal for luminescence applications because the sample signal is greatly diminished due to the non-reflective nature of the plastic.

Regardless of color, the cost of opaque plates as compared to conventional transparent plate is substantial. Opaque plates currently cost approximately $5 to $6 each, as compared to transparent plates which normally retail for less than half that amount. For example, sterile opaque 96-well plates and lids are offered by DynaTech Laboratories at a combined retail cost of $286 per set of 50, or $5.72 per each. Similarly treated transparent 96-well plates with lids are manufactured by Corning (Corning, N.Y.) and can be purchased at a retail cost of $110 per 50, or $2.20 per each.

In addition to their cost, opaque plates impose technical limitations not associated with clear multi-well plates. For example, many researchers desire to expedite their assay operations and reduce the cost of materials by culturing cells directly in the wells of the microplate used to perform the final assay. Opaque plates are inferior for this purpose because:

i) cultured cells cannot be viewed or photographed through the opaque plate;
ii) the composition and surface characteristics of opaque plastics are different from those of standard cell culture-grade plasticware, and have undetermined effects on cell adhesion and growth characteristics; and
iii) sterile, cell-culture grade opaque plates and covers (packaged separately) are not widely available.

One manufacture (Packard, Meridian, Conn.) recognized the technological problems associated with opaque plates and responded by developing a specialty plate consisting of an opaque plastic body with a clear plastic bottom (sold under the name "View Plate", product #600-5181). However, the availability of such specialty plates is limited, and the high price ($6 each) of such a consumable product is generally prohibitive for high-throughput users in both academic and private laboratories.

As is evident from the above discussion, there is a substantial need for luminescence assays which retain the speed and sensitivity of known luciferase assays, yet can be performed in conventional, cell-culture grade multiwell plates manufactured from optically-clear plastic.

The present invention provides such luminescence assays. The invention relates to luminescence assays which include at least one reagent which rapidly quenches a given luminescence reaction, thereby allowing subsequent wells to be assayed without refractive or reflective cross-talk between wells.

The 1991 publication of Thompson et al. presents findings on the use of substrate analogs (benzothiazole, phenylbenzothiazole, and hydroxy-phenylbenzothiazole) to induce conformational changes in firefly luciferase. Thompson demonstrates that, when bound to the luciferase enzyme, said chemical compounds provide increased in vivo and in vitro stability to the luciferase enzyme by conferring greater resistance to proteolytic degradation. Though analogs to beetle luciferin are inhibitors of firefly luciferase activity, the assay of luciferase activity from treated samples was performed using diluted cellular extracts containing sub-inhibitory concentrations of the various residual substrate analogs.

U.S. Pat. No. 4,235,961, issued Nov. 25, 1980, to A. T. Lundin, describes a method for the photometric determination of subunit B of creatinine kinase. The assay proceeds in the presence of the L-luciferin enantiomer of the natural beetle luciferase substrate (D-luciferin), which acts as a competitive inhibitor of the luciferase/D-luciferin reaction. Inhibition of the photometric reaction provides a more continuous emission of light from the sample, thereby allowing the kinetics of creatine kinase reaction to be studied.

U.S. Pat. No. 4,390,274, issued Jun. 28, 1983, to Berthold et al., describes a photometric assay in which an additional luminescence substrate is added to a sample after a first experimental photometric measurement is taken. A second photometric measurement is then taken. The added substrate is chemically distinct from the experimental substrate being measured, but is a reaction partner in the same luminescence reaction system that is photometrically determined in the first measurement. The added substrate is used for internal standardization of each sample.

Various other publications describe chemical compounds which will reduce the luminescence of a luciferase reactions, but in none of these is this reduction of purposeful value in itself. The 1970 publication of Denburg and McElroy presents findings on the interaction of selected anions as inhibitors of the firefly luciferase luminescent reaction. Thiocyanate, iodide, nitrate, bromide and chloride are found to have varying inhibitory interaction with the luciferase enzyme. The 1970 publication of Lee et al. and the 1969 publication of Denburg et al. presents findings on various competitive inhibitors of the firefly luciferase luminescent reaction.

The concept of a dual-enzyme reporter system relates to the simultaneous use, expression, and measurement of two individual reporter enzymes within a single system. In genetic reporting, examples that currently benefit from dual-reporter assays include individual cells or cell populations (such as cells dispersed in culture, segregated tissues, or whole animals) genetically manipulated to simultaneously express two different reporter genes. Most frequently, the activity of one gene reports the impact of the specific experimental conditions, while the activity of the second reporter gene provides an internal control by which all sets of experimental values can be normalized.

Cell-free reconstituted systems that may benefit from dual-enzyme reporter technology are cellular lysates derived for the simultaneous translation, or coupled transcription and translation, of independent genetic materials encoding experimental and control reporter enzymes. Immuno-assays may, likewise, be designed for dual-reporting of both experimental and control values from within a single sample.

Currently, genes encoding firefly luciferase (luc), chloramphenicol acetyl transferase (CAT), beta-galactosidase (lacZ), beta-glucuronidase (GUS) and various phosphatases such as secreted alkaline phosphatase (SEAP) and uteroferrin (Uf; an acid phosphatase) have been combined and used as co-reporters of genetic activity. The following references provide representative examples of these various reporter genes used in combined form for the purpose of dual-reporting of genetic activity: luc and GUS: Leckie, F., et al., 1994; luc and CAT, and luc and lacZ: Jain, V. K. and Magrath, I. T., 1992; CAT and lacZ: Flanagan, W. M. et al., 1991; SEAP and Uf: Kondepudi, et al. , 1994.

The perfomance of any dual-enzyme reporter assay is limited by the characteristics of the constituent enzyme chemistries, and the ability to correlate their respective resulting data sets. Quantifying the combined expression of any two of the above reporters from within a single cell lysate necessitates splitting the sample so that the activity of each reporter can be assayed independently. Hence, the disparate enzyme kinetics, assay chemistries and incubation requirements, of these various reporter enzymes makes it impossible to combine them into an integrated, single-tube, dual-reporter assay format. An ideal dual-reporter system would be comprised of two enzyme assays with compatible chemistries, and identical temperature and handling conditions, speed, sensitivity, and instrumentation required for detection.

SUMMARY OF THE INVENTION

The present invention is drawn to single enzyme and integrated dual-enzyme luminescence assays which utilize one or more reagents to rapidly and efficiently quench enzyme-mediated luminescent reactions.

An enzyme-mediated luminescence reaction is any chemical reaction which yields photons as a consequence of the reaction, and uses an enzyme to effectively enable the reaction. Examples are luciferases isolated from a variety of luminous organisms, such as the firefly luciferase of *Photinus pyralis* or the Renilla luciferase of *Renilla reniformis*.

Luciferases are enzymes found in luminous organisms which catalyze luminescence reactions. They are organized into groups based on commonallies of their luminescence reactions. All luciferases within a group are derived from related luminous organisms, and all catalyze the same chemical reaction. Examples are beetle luciferases, which all catalyze ATP-mediated oxidation of the beetle luciferin; and anthozoan luciferases which all catalyze oxidation of coelenterazine (Ward, 1985). With the technical capabilities of molecular biology, it is possible to alter the structure of a luciferase found in nature to yield a functional equivalent thereof. A functional equivalent is an enzyme that maintains the ability to catalyze the same luminescence reaction, and thus it remains in the same group of enzymes. An example is a genetic fusion to another protein to yield a bifunctional hybrid protein (Kobatake, et al., 1993). Other enzymes that are not luciferases can mediate a luminescence reaction using synthetic substrates. Examples are horseradish peroxidase, which catalyzes a reaction involving luminol (Thorp et al., 1986); and alkaline phosphatase, which catalyzes a reaction with adamantyl 1,2-dioxetane phosphate (Schaap et al., 1989).

A luminescence reporter is a molecule which mediates a luminescence reaction, and by doing so yields information about the state of a chemical or biochemical system. Examples are genetic reporters (Wood, 1995), immunoassay reporters (Bronstein et al., 1991), and ATP reporters (Schram, 1991). Enzymes are proteins which catalyze a chemical transformation, and thus are not changed by that transformation. Because the enzyme is regenerated at the conclusion of the transformation, it is available for additional cycles of transformation; enzymes thus have the capacity for substrate turnover. This property allows the capacity for continuous luminescence in enzyme-mediated luminescence reactions. Some proteins, such as aequorin (Ward, 1985), do not allow substrate turnover, and this do not support continuous luminescence. These proteins are not enzymes and are outside the scope of this invention. If the properties of such proteins could be altered to allow substrate turnover, they would then become enzymes and hence would be included in this invention. The enzyme in an enzyme-mediated luminescence reaction is said to effectively enable the reaction when the majority of the luminescence generated in the reaction follows as a consequence of the action of the enzyme.

In a first embodiment, the present invention relates to single-reporter luminescence assays using reagents which non-specifically extinguish luminescence enzymatic reactions. In this embodiment of the invention, referred to herein as general enzymatic quenching, an enzyme-mediated, luminescence reaction is first initiated by addition of the proper initiating reagent or reagents into the experimental system. The luminescence signal produced in the experimental system is then measured using a photomultiplier tube, or any other suitable means therefor. The enzymatic reaction is then quenched by the addition of a general quench reagent. The quench reagent should diminish the luminescence signal by 1,000-fold within a relatively short time interval after introduction of the quench reagent. The luminescence signal should preferably be quenched within 30 seconds, and more preferably still within about 10 seconds. This allows numerous samples to be assayed very quickly. The preferred formulation for a general quench reagent will diminish the luminescence signal of a given enzymatic reaction by 100,000-fold.

By extinguishing the luminescence signal from within the sample, addition of the general quench reagent prevents light from previously-activated samples from interfering with light measurements in subsequently-activated samples in a multisample assay format.

Examples of types of general quench reagents include organic reagents (e.g., isopropanol), detergents (e.g., SDS), and structural intercalaters such as hydrophobic dyes. Such general quench reagents are ideally suited for use with automatic injectors and in microliter plates (both opaque and clear) such as conventional 96-well plates.

Because the quench reagent effectively extinguishes the luminescence signal from within a sample., multiple luminescence assays can be performed within a clear multi-well plate without refractive cross-talk between samples.

Moreover, researchers who choose to perform low-activity luminescence assays in white plates because of their greater reflectivity are also benefitted by the present invention because it eliminates unacceptable levels of reflected background light.

In a second embodiment, the present invention relates to dual-reporter luminescence assays utilizing reagents which selectively extinguish one luminescence reporter enzyme while simultaneously initiating another distinct enzyme-mediated luminescence reaction. Here, the quench reagent is referred to as a specific quench reagent because the reagent quenches only a specifically selected enzyme-mediated luminescence reaction. When the reagent is further formulated to allow simultaneous initiation of a second enzyme-mediated luminescence reaction, the reagent is referred to as a "quench-and-activate" reagent. This assay allows the sequential measurement of two separate and distinct luminescence reporters within one sample. As a result, one of the luminescence reporters can be used as an internal standard, while the other is used to reporter the impact of the experimental variables.

In the dual-reporter assay, two distinct enzyme reporters are used. The two enzymes respond differently to various reagents, thereby allowing either of the enzyme-mediated luminescence reactions to be selectively quenched. In operation, one of the two enzyme-mediated luminescence reactions is first initiated by addition of the proper initiating reagent or reagents into the experimental system. The luminescence signal produced by the first enzymatic reaction is then measured as described above. The first enzymatic reaction is then specifically and selectively quenched by adding a quench-and-activate reagent which simultaneously quenches the first enzymatic reaction and initiates the second enzymatic reaction. The luminescence signal produced by the second enzymatic reaction is then measured in the same fashion as the first reaction. In this manner, two luminescence reactions, mediated by two different enzymes, can be assayed sequentially in time, within the same reaction vessel.

Illustratively, firefly luciferase will be selectively quenched using metal chelators, substrate analogs (e.g., luciferin analogs such as dehydroluciferin), and pyrophosphate. Absolute quenching of the luminescence reaction is not necessary so long as the relative inhibition is large, preferably 100,000-fold, and reproducible. These quench reagents are specific for firefly luciferase or other beetle luciferases, and will have no effect on luciferase reporters of other types present in the experimental system. Therefore, the first luciferase reaction, in this example a firefly luciferase-mediated reaction, can be selectively quenched, while allowing a second luciferase-mediated reaction, such as a Renilla luciferase,-mediated reaction, to proceed without inhibition. It is understood that the above example is for illustration purposes only, and is not limiting in any fashion.

As noted above, because the specific quench-and-activate reagents selectively quench one luminescence reaction while, at the same time, triggering the onset of a second luminescence reaction, different luminescence markers (e.g., an experimental reporter and a control reporter that provides an internal standard) can now be quantified consecutively within the same sample. This strategy greatly expedites the operation of reporter multiplexing to provide quick, automatable, accurate, and reproducible results using standard multi-well plates and instrumentation. For instance, in a more specific example of the dual-reporter assay described above, the luminescence chemistries of beta-galactosidase, beta-glucuronidase, alkaline phosphatase or other luciferases can be utilized in a dual-reporter luminescence assay with firefly luciferase. One of the two luminescent enzymes acts as an internal standard, while the other functions as an experimental marker for gene activity.

To summarize, the present invention describes general and specific reagents formulated to provide rapid, efficient, and reproducible quenching of luminescence reactions. This capability affords two distinct advantages over conventional luminescence assays:

i) it removes the current burden of using expensive, technically-limited plasticware for microplate luminescence assays; and ii) it provides the capability to perform multiple luminescence reactions from one sample preparation, contained within a single sample tube, using a single instrument for quantification of each luminescent signal.

The present invention therefore provides the technology needed to implement high-throughput automated assays based on enzyme-mediated luminescence reporter systems, using conventional transparent or opaque multi-well plates.

The invention also includes quench reagents and assay kits for analyzing samples using enzyme-mediated luminescence reactions.

The present invention is ideally suited for luminescence reactions because the experimental entity being measured, photons, are transient in existence. Therefore, quenching the enzymatic reaction which causes the production of photons immediately diminishes the product photons present in the sample. In other words, once the luminescence measurement is taken, and the luciferase reaction is quenched, the fleeting nature of photons means there is no build-up of product photons in the sample. In essence, luminescence reactions can be "turned off" without leaving an accumulation of the experimental or control signal (i.e., photons) within the sample.

The same cannot be said of analogous enzymatic reactions in which the buildup of a stable chemical product is measured, or the slow decay of an accumulated chemical product is measured. Here, quenching the enzymatic reaction leading to the chemical product still leaves a large accumulation of the chemical product within the sample, leading to interference with other assays being simultaneously or sequentially taken from the sample.

In light of the above discussion, it is an object of the present invention to provide reagents which non-specifically quench enzyme-mediated luminescence reactions.

It is another object of the present invention to provide reagents which specifically quench a selected enzyme-mediated luminescence reaction without affecting other distinct enzyme-mediated luminescence reactions.

Yet another object of the present invention is to provide a single-reporter, enzyme-mediated luminescence assay utilizing a reagent which non-specifically quenches enzyme-mediated luminescence reactions.

Still another object of the invention is to provide a dual-reporter, enzyme-mediated luminescence assay utilizing a reagent which specifically quenches a first chosen enzyme-mediated luminescence reaction, while simultaneously initiating a second and distinct enzyme-mediated luminescence reaction.

A still further object of the present invention is to provide a luminescence assay which can be performed in transparent or opaque multi-well plates without refractive or reflective cross-talk light contamination between wells.

A still further object of the present invention is to provide single and dual-reporter luminescence assays which are automatable using conventional laboratory instrumentation and disposable plasticware.

These and other objects of the present invention will become clear upon a complete reading of the "Detailed Description," and claims, below.

DETAILED DESCRIPTION OF THE INVENTION

Definitions

Figure 1:
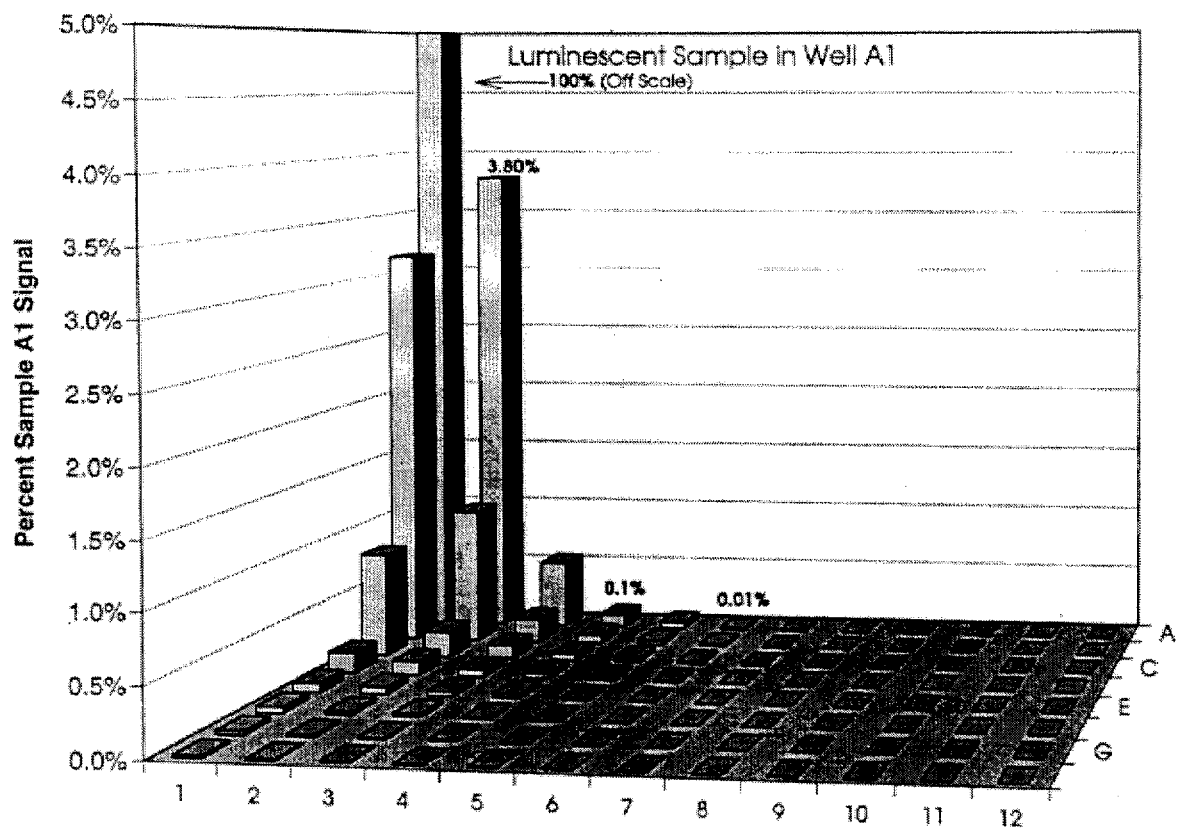
FIG. 1 is a three-dimensional graph showing signal cross-talk radiating from a single luminescent sample within a clear plastic, 96-well microplate.

For purposes of brevity and clarity, unless otherwise noted the terms "luciferase" and "luciferin" as used herein shall mean any type of luciferase originating from any natural, synthetic, or genetically-altered source, including, but not limited to: luciferases isolated from the firefly *Photinus pyralis* or other beetle luciferases (such as luciferases obtained from click beetles (e.g., *Pyrophorus plagiophthalamus*.) or glow worms (Pheogodidae spp.)), the sea pansy *Renilla reniformis*, the ostracod *Vargula hilgendorfii*, the limpet *Latia neritoides*, and bacterial luciferases isolated from such organisms as *Xenorhabdus luminescens*, and *Vibrio fisherii*; and their respective substrates and functional equivalents thereof.

The names of some of the chemicals listed in Tables 1–5, and referred to in various sections of the specification and claims, are presented in abbreviated form. The following definitions of chemical abbreviations are therefore provided to assist in providing a clear and consistent understanding of the scope and detail of the terms:

| Abbreviated Designation | Chemical |
|---|---|
| APMBT | 2-(4-aminophenyl)-6-methylbenzothiazole |
| APO-10 | Dimethyldecylphosphine Oxide |
| ATP | Adenosine 5'-Triphosphate |
| Beetle Luciferin | 2-(6'-Hydroxy-2'-benzothiazolyl)-$\Delta^2$-thiazoline-4-carboxylic acid |
| BSA | Bovine Serum Albumin |
| BT | Benzothiazole |
| HAc | Acetic acid |
| PBT | 2-Phenylbenzothiazole |
| CDTA | trans-1,2,-Diaminocyclohexane-N,N,N',N'-tetraacetic acid |
| Dehydroluciferin | 2-(6'-Hydroxy-2'-benzothiazolyl)-thiazole-4-carboxylic acid |
| DTT | Dithiothreitol |
| EDTA | Ethylenediaminetetraacetic acid |
| HPBT | 2(O-Hydroxyphenyl)benzothiazole |
| HEPES | N-2-Hydroxyethylpiperazine-N'-2-ethansulfonic acid |
| IFP Ink | India Fountain Pen Ink |
| Na$_4$PPi | Tetrasodium Pyrophosphate |
| or-ATP | Adenosine 5'-Triphosphate 2',3'-acyclic dialcohol, Periodate Oxidized, Borohydride Reduced |
| SDS | Sodium Dodecyl Sulfate |

The present invention includes a method of assaying enzyme-mediated luminescence reactions which comprises the steps of initiating at least one enzyme-mediated luminescence reaction, quantifying luminescence energy produced by the luminescence reaction, and quenching photon emission from the enzyme-mediated luminescence reaction by introducing at least one quench reagent to the luminescence reaction.

The enzyme-mediated luminescence reaction may be a luciferase-mediated reaction, and in that case, it is preferred that the reaction is quenched with a quench reagent capable of reducing photon emissions from the luciferase-mediated luminescence reaction by a factor of at least 1,000-fold.

The luciferase-mediated reaction may be quenched with a number of different reagents, including one or more quench reagents selected from the following group of compounds: iodide, iodine, sulfate, nitrate, iso-propanol, 2-(4-aminophenyl)-6-methylbenzothiazole, dimethyldecylphosphine oxide, pyrophosphate, benzothiazole, 2-phenylbenzothiazole, n-butanol, trans-1,2,-diaminocyclohexane-N,N,N',N'-tetraacetic acid, 2-(6'-hydroxy-2'-benzothiazolyl)-thiazole-4carboxylic acid, ethylenediaminetetrethylenediaminetetraacetic acid, 2(o-hydroxyphenyl)benzothiazole, India foutain pen ink adenosine 5'-triphosphate 2', 3'-acyclic dialcohol periodate oxidized borohydride reduced, sodium dodecyl sulfate, citric acid, Tween®20, Triton®X-100, and mixtures thereof.

The quench reagents listed immediately above may be formulated into preferred quench reagent compositions including mixtures selected from the following group: SDS and NaI; I$_2$ and I; Na$_4$PPi and NaI; Na$_4$PPi, CDTA, and APMBT; Na$_4$PPi, APMBT, and Na$_2$SO$_4$; Na$_4$PPi, CDTA, APMBT, and Na$_2$SO$_4$; Na$_4$PPi and APMBT; Na$_4$PPi and iso-propanol; IFP Ink and APMBT; APMBT and CDTA; IFP Ink and CDTA; IFP Ink and Na$_4$PPi; SDS and NaI; Tween®20 and NaI; Tween®20, NaI, and n-butanol; Triton®X-100 and NaI; and mixtures thereof.

The preferred final assay concentrations of the compounds in the above mixtures are as follows: 0.33% (w/v) SDS and 170 mM NaI; 1.3 mM I$_2$ and 45.5 mM NaI; 25 mM Na$_4$PPi and 100 mM NaI; 7.5 mM Na$_4$PPi, 5.0 mM CDTA and 12.5 µM APMBT; 7.5 mM Na$_4$PPi, 12.5 µM APMBT and 200 mM Na$_2$SO$_4$; 7.5 mM Na$_4$PPi, 5.0 mM CDTA, 12.5 µM APMBT and 200 mM Na$_2$SO$_4$; 6.3 mM Na$_4$PPi and 3.1 µM APMBT; 6.3 mM Na$_4$PPi and 3.1% (v/v) iso-propanol; 1/3,000xIFP Ink and 3.1 µM APMBT; 3.1 µM APMBT and 7.9 mM CDTA; 1/3,000xIFP Ink and 6.2 mM CDTA; 1/3,000xIFP Ink and 3.1 mM Na$_4$PPi; 0.33% (w/v) SDS and 170 mM NaI; 0.33% (v/v) Tween®20 and 170 mM NaI; 0.33% (v/v) Tween®20, 170 mM NaI, and 0.83% (v/v) n-butanol; and 0.33% (v/v) Triton®X-100 and 170 mM NaI.

Among luciterases specifically, the method of the present invention may be used to assay luminescence reactions mediated by beetle luciferases, including *Photinus pyralis* luciferase, and *Pyrophorus plagiophthalamus* luciferase. Another luciferase which is widely used in the field of research, and which may be assayed using the present invention is the reaction catalyzed by *Renilla reniformis* luciferase.

The present invention also includes a dual-reporter method for assaying enzyme-mediated luminescence reactions in which a first enzyme-mediated luminescent reaction mediated by a first enzyme is initiated, and the luminescent energy of the first reaction recorded. This is followed by introduction of a quench-and-activate composition capable of selectively quenching the first enzyme-mediated luminescence reaction and simultaneously initiating a second enzyme-mediated luminescence reaction which is distinct from the first enzyme-mediated luminescence reaction. The luminescent energy produced by the second enzyme-mediated luminescence reaction is then measured. In an optional step, the second enzyme-mediated luminescent reaction may then subsequently be quenched by the addition of a second quenching reagent.

The invention also includes a single-reporter and a dual-reporter assay kits which contain reagents for performing the subject method. The single-reporter kit comprises at least one quench reagent composition capable of quenching photon emission from an enzyme-mediate luminescence reaction, preferably by a factor of at least 1,000-fold. The at least one quench reagent composition is disposed within a suitable first container. At least one functional enzyme substrate corresponding to the enzyme-mediated luminescence reaction being assayed is included in the kit, along with a suitable second container into which the at least one functional enzyme substrate is disposed. The kit also includes instructions on its use.

The dual-reporter kit includes a first functional enzyme substrate corresponding to a first enzyme-mediated luminescence reaction being assayed contained within a suitable first container. A quench-and-activate composition comprising quench reagents capable of quenching photon emission from the first enzyme-mediated luminescence reaction by a factor of at least 1,000-fold, and a second and distinct functional enzyme substrate corresponding to a second and distinct enzyme-mediated luminescence reaction are contained within a suitable second container. The dual-reporter kit also includes instructions for its use. Optionally, the dual-reporter kit may also contain a second quench reagent contained within a suitable third container, the second quench reagent capable of quenching the second and distinct enzyme-mediated luminescent reaction.

The present invention also includes enzyme-mediated luminescence reaction quench reagents which are capable of reducing photon emissions from enzyme-mediated luminescence reactions The impact of light refraction on the accurate quantification of luminous reactions contained in clear plastic multi-sample plates As a research tool for molecular biologists, luminescent enzyme reporter systems are more sensitive than the other, more traditional, enzyme reporter systems. Luciferuse assays, in particular, are also much more rapid than those of other enzyme reporter systems. These features make luminescence-generating enzymes the preferred reporters of genetic and physiological activity.

New applications for luminescent reporters are now emerging based on high throughput assays utilizing 96-well plastic microplates. However, refractive properties of clear plastics cause extreme light cross-talk between samples, compromising the sensitivity of luciferuse assays. The power of luminescent reporter systems is greatly diminished if signal interference contributed from preceding luminescent reactions exceeds 0.1%.

Figure 2:
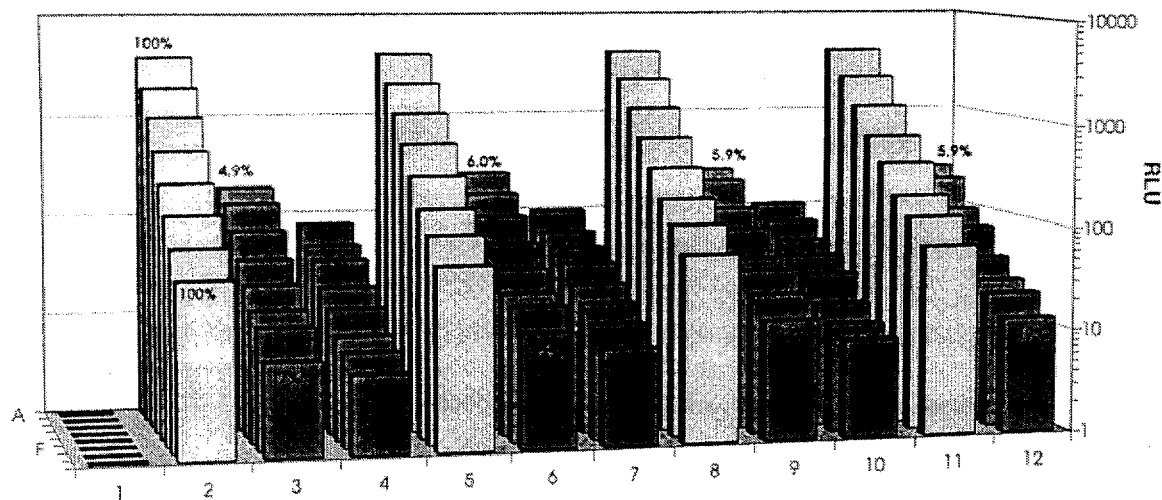
FIG. 2 is a three-dimensional graph showing the cumulative nature of signal cross-talk radiating from multiple luminescent samples within a clear plastic, 96-well microplate.

FIGS. 1 and 2 demonstrate that light refraction from relatively bright luminescent reactions contained in clear multi-well plates easily contributes greater than 0.1% signal interference to even distant sample wells. Indeed, background interference exceeds 6% in wells that are adjacent to single-sample reactions with high luminescent activity. Cumulative background interference due to light refraction from several luminescent samples is even much greater. Thus, despite their other technological and economic advantages, multi-well plates of clear plastic are currently unsuitable for high throughput assays using luminescent assays.

FIG. 1 graphically depicts the extreme refractive properties of clear polystyrene. A cell-free extract of firefly luciferase-expressing Chinese hamster ovary (CHO) cells was prepared, as described in full below, and used to demonstrate the general phenomenon of light channeling through a clear plastic multi-well plate to produce cross-talk light interference in neighboring sample wells. 20 μl of the extract was combined with 100 μl of Luciferase Assay Reagent (Promega Corp., Madison Wis.) in sample well 6D of a clear polystyrene 96-well plate. Luminescence from the single firefly luciferase reaction was then quantified in all 96 sample wells using a Luminoskan RT luminometer (Labsystems; Helsinki, Finland) programmed to integrate photon emission over a 4 second period. Although only well 6D contained an active luciferase reaction, significant signal (>0.1%) was measured in empty sample wells extending five columns distant from the luminescent source.

Cross-talk between multiple luminescent samples in distant wells of a clear plastic micro-well plate causes cumulative signal interference between sample wells, as is shown in FIG. 2. Here, a lysate of CHO cells transfected with pGL3-Control (a firefly luciferase expression plasmid available from Promega Corp, product #E1741) was prepared as eight consecutive 1:2 dilutions using Reporter Lysis Buffer (Promega Corp.) containing 1 mg BSA/ml. 20 μl of each luciferase dilution was dispensed into sample wells A–H of columns 2, 5, 8 and 11 of a Corning clear polystyrene 96-well plate. A Lab Systems Luminoskan RT luminometer was used to sequentially inject Promega Luciferase Assay Reagent and quantify light emission from each individual sample well, as described previously.

FIG. 2 is a plot of the Relative Light Units (RLU) measured for each well of the 96-well plate. A high percentage of refracted and scattered light is measured in the columns of wells devoid of sample that are adjacent to columns with actively luminescent reactions. Cumulative light cross-talk ranges from 5–6% in wells A:3, 6, 9 and 12 (i.e., those wells containing only the added BLA Reagent which are immediately adjacent to wells containing high level luminescent reactions), whereas cross-talk measured in wells H:3, 6, 9 and 12 (i.e., those wells containing only the added BLA Reagent which are immediately adjacent to wells containing low light reactions) exceeds 17%. Clearly, when bright and dim luminescent reactions are interspersed on a single clear plastic multi-well plate, the negative affects of sample cross-talk will have much greater impact on the accurate measurement of low-light samples. Since the luminometer follows a top-to-bottom path in processing columns of samples, wells A1–H1 are measured before the first luminescent reaction (well A2) is initiated by the injection of Promega Luciferase Assay Reagent. Thus, wells in column 1 provide a convenient control to confirm the absence of background signal caused by plastic phosphorescence and/or instrument noise.

As noted above, it is an object of the present invention to allow luminescence reactions to be carried out in conventional 96-well, clear plastic microtiter plates. As is convincingly shown in FIGS. 1 and 2, accurate luminescence measurements cannot be obtained in conventional clear multi-well plates due to signal cross-talk caused by light which is refracted through the clear plastic of the plate into surrounding wells. The present invention solves this problem.

In a first embodiment of the present invention, a luminescence assay utilizing a general quench reagent is described. By the term "general quench reagent" is meant a reagent which non-specifically quenches luminescence reactions, preferably luciferase-mediated luminescence reactions without regard to the source of the luciferase.

To effectively eliminate light refraction between luminescent reactions contained in neighboring wells of clear plates the general quench reagent should provide a minimum 1,000-fold reduction in luminescent signal for each sample. Due to the cumulative nature of light cross-talk from many individual luminous reactions, it is preferred that the: general quench reagent provide a 100,000-fold decrease in the light emissions from each luminescence reaction.

The mechanism by which general quench reagents function is not critical to the functionality of the present invention. For ease of designation, applicants have categorized some quench reagents according to their putative mechanisms of inhibition. For instance, as shown in Table 1, which lists several general quench reagents, some reagents, such as dehydroluciferin, are considered to be substrate analogs. These reagents inhibit enzyme reactions by binding at the enzyme binding site of the substrate, thereby preventing the enzyme from binding with its intended substrate.

General quench reagents are also believed to exert their inhibitory effects by anionic interactions, or by denaturation of the proteinaceous enzyme. As noted above, however, the actual mechanism of the quenching phenomena is not critical to the present invention, so long as the quenching is large and reproducible.

TABLE 1

Evaluation of Compounds for their Ability to Quench the Luminescent Reaction of Firefly Luciferase

| Functional Type of Inhibitor | Beetle Luciferase Quench (BLQ) Reagent Tested | Representative Assay Concentration of Reagent Tested | Percent (%) Residual Firefly Luciferase Activity |
|---|---|---|---|
| Substrate Analogs | Dehydroluciferin | Saturating | 0.064 |
|  | APMBT | 7.6 µM | 0.33 |
|  | or-ATP | 7.6 mM | 0.78 |
|  | BT | 3.0 mM | 2.3 |
|  | PBT | 0.15 mM | 7.5 |
|  | HPBT | 30 µM | 44 |
| Anionic Interaction | NaI | 400 mM | 0.078 |
|  | $Na_4PPi$ | 31 mM | 0.12 |
|  | $NaNO_3$ | 400 mM | 2.1 |
|  | $K_2HPO_4$ | 190 mM | 8.3 |
|  | NaCl | 400 mM | 8.3 |
|  | $Na_2SO_4$ | 400 mM | 10 |
| General Protein Denaturants | SDS | 0.3% (w/v) | 0.079 |
|  | APO-10 | 1.0% (w/v) | 1.9 |
|  | iso-Propanol | 14.4% (v/v) | 2.3 |
| Other | IFP Ink | 1/1,280x | 0.015 |
|  | Household Bleach | 15.7% (v/v) | 0.078 |
|  | CDTA | 15.4 mM | 0.10 |
|  | EDTA | 22.7 mM | 0.13 |
| Selected Combined Formulations | $Na_4PPi$, NaI | 25 mM, 100 mM | 0.000043 |
|  | $Na_4PPi$, CDTA, APMBT, $Na_2SO_4$ | 7.5 mN, 5.0 mM, 12.5 µM, 200 mM | 0.00035 |
|  | $Na_4PPi$, CDTA, APMBT | 7.5 mM, 5.0 mM, 12.5 µM | 0.00097 |
|  | $Na_4PPi$, APMBT, $Na_2SO_4$ | 7.5 mM, 12.5 µM, 200 mM | 0.0011 |
|  | $Na_4PPi$, APMBT | 6.3 mM, 3.1 µm | 0.0035 |
|  | APMBT, IFP Ink | 3.1 µM, 1/3,000x | 0.0037 |
|  | APMBT, CDTA | 3.1 µM, 7.9 mM | 0.0041 |
|  | IFP Ink, CDTA | 1/3,000x, 6.2 mM | 0.0058 |
|  | IFP Ink, NaPPi | 1/3,000x, 3.1 mM | 0.0073 |
|  | iso-Propanol, $Na_4PPi$ | 3.1% (v/v), 6.3 mM | 0.15 |
|  | $I_2$NaI | 1.3 mM, 45.5 mM | 0.27 |
|  | iso-Propanol, APMBT | 3.1% (v/v), 3.1 µM | 0.35 |
| Control Reaction: No inhibitor Added |  |  | (100%) |

Although quench reagents comprising a single chemical entity are shown in Table 1, superior results are obtained by using a quench reagent which includes a number of different chemical entities. Therefore, it is preferred that the quench reagent be a combination of ingredients so as to result in the most effective and expedient inhibition of luminescence reactions in general, and luciferase-mediated reactions in particular.

Of the various general quench reagents listed in Table 1, the preferred general quench reagent is 50 mM tetra sodium pyrophosphate, 200 mM sodium iodide, and 10 mM HEPES, pH 6.5. This combination of ingredients rapidly and effectively quenches luminescent reactions from beetle luciferases. When specifically applied in a 1:1 volume ratio to firefly luciferase-mediated reactions, this combination leaves a residual luminescence signal which is only 0.000043% of the original signal.

Figure 3:
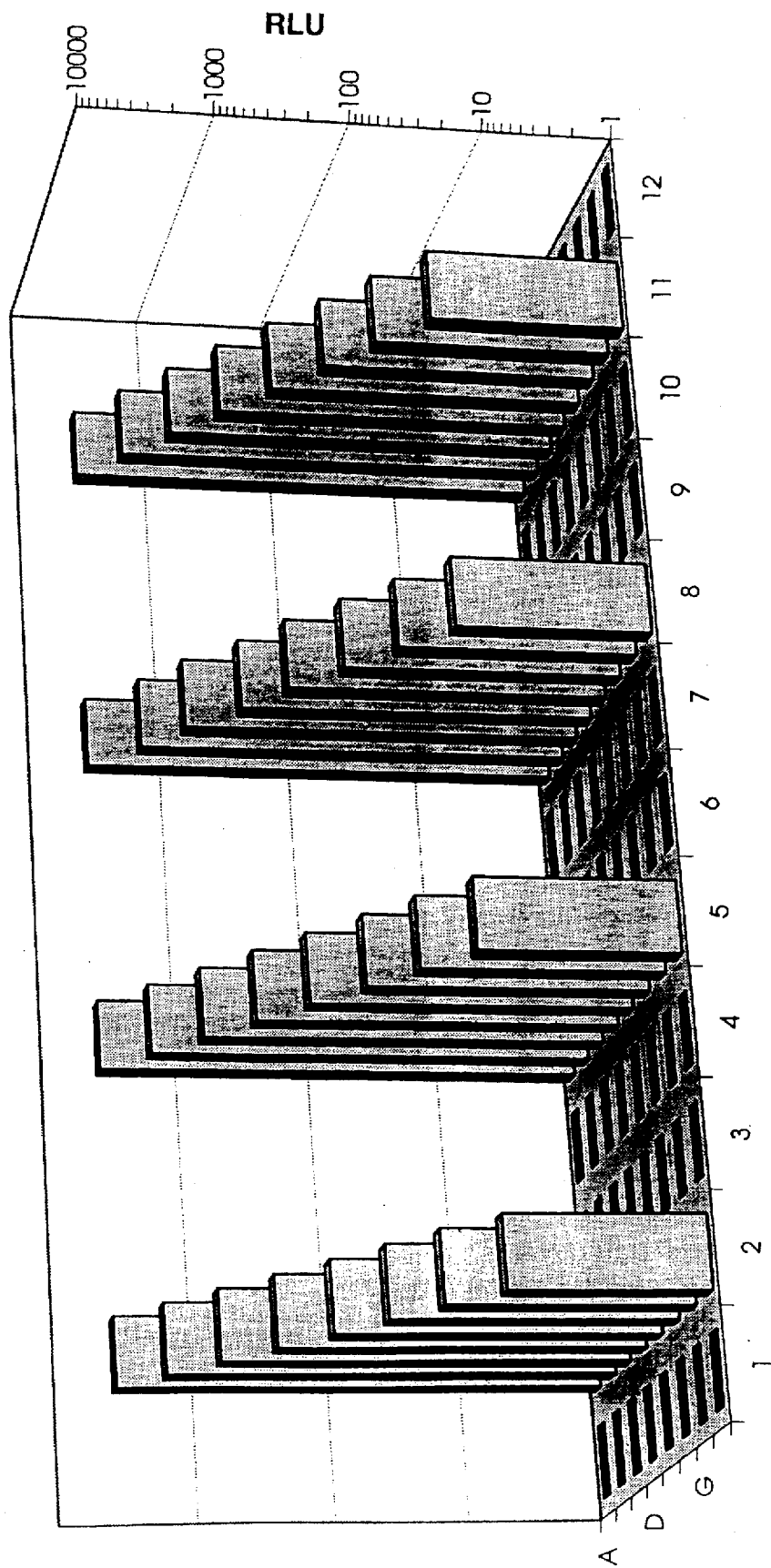
FIG. 3 is a composite of two three-dimensional graphs showing A) the phenomenon of signal interference between neighboring samples in a clear plastic multi-well plate, and B) the elimination of signal cross-talk by the use of the present invention.

FIG. 3-B shows the results of an experiment identical to that shown in FIG. 2 with the exception that after each luminescence reading, an equivalent volume of a general quench reagent consisting of 50 mM $Na_4PPi$, 200 mM NaI, and 10 mM HEPES (pH 6.5) was injected into each well prior to activating the luminous reactions contained in subsequent wells. As is clearly shown by comparing FIG. 3-B and FIG. 3-A (the same reaction without quench reagent), cross-talk between the luminous wells and the dark wells has been completely eliminated.

The impact of adding the general quench reagent on the accuracy of quantifying luminescence assays performed in clear plastic multi-well plates is illustrated in Table 2. These data were obtained by placing serial dilutions of luciferase solutions into standard clear polystyrene 96-well plates, and measuring light intensity in the manner described herein. Average luminescence values were determined for the four luminescent samples contained in each row of the multi-well plate of FIG. 3-A, in which all luminescent reactions remained unquenched, and therefore continued to emit persistent luminescence. Average luminescence values were also determined for the four samples in the respective wells of the multi-well plate of FIG. 3-B, in which all previous luminescent reactions were quenched. The difference between respective average values

| Samples in Row | Average Luminescence Values Measured from ... | | Percent Error Contributed from |
|---|---|---|---|
|  | Non-quenched Luminous Reactions | quenched Luminous Reactions | Non-Quenched Luminescent Samples |
| A | 4,023 | 3,948 | 1.9% |
| B | 2,183 | 1,971 | 11% |
| C | 1,177 | 1,005 | 17% |
| D | 617 | 482 | 28% |
| E | 333 | 243 | 37% |
| F | 176 | 119 | 48% |
| G | 106 | 59.7 | 77% |
| H | 58.7 | 28.6 | 105% | allowed for the determination of percent error in measured signal for each sample contained in the non-quenched multi-well plate. Table 2 convincingly demonstrates that relative error due to cumulative signal cross-talk becomes increasingly significant, as would be expected, when quantifying low-activity luminous reactions.

Reagent formulation for general quenching of luciferase-catalyzed luminescent reactions Numerous chemical compounds were tested individually and in combination for their ability to rapidly quench luciferase catalyzed luminescent reactions. Table 1 and Table 3 present the potency of quenching firefly and Renilla luciferases, respectively, for representative concentrations of the compounds tested. The percentage of residual luminescent signal measured after addition of the test compound is indicative of its quenching efficiency. Whether used individually or in combination at varying concentrations, useful quench formulations should be capable of reducing luminescence from the luciferase reactions by 1,000-fold, i.e., to 0.1% of the starting luminescent emission.

Firefly luciferase reactions were performed using the Luciferase Assay Reagent and protocol included in the Luciferase Assay System kit commercially available from Promega Corp. (Madison, Wis. Kit#4030). Luminescence from both the control and quenched firefly luciferase reactions (Table 1) were performed using an extract of CHO cells expressing pGL3-Control, prepared as described below. Control reactions were conducted by dispensing 10–20 µl of extract into a luminometer tube containing 100 µl Promega Luciferase Assay Reagent and quantifying light emission. Experimental reactions were conducted by adding into individual luminous reactions 50 µl of a candidate quench reagent, here given the generic designation of Beetle Luciferase Quench(BLQ) Reagents. Formulations comprising two or more chemicals were conducted similarly, except that the volume of added quench reagent was increased to 100 µl. Luminescent intensity of the control and quenched firefly luciferase reactions were quantified by integrating photon flux over a 10 second period using a Turner Designs (Sunnyvale, Calif.) Model 20e luminometer.

Renilla luciferase reactions were performed by adding 100 µl of purified Renilla luciferase (typically diluted to 0.3 µg per ml in 75 mM HEPES, 0.02% BSA; pH 8) to a luminometer tube containing an equal volume of Renilla substrate solution (7.5 mM sodium acetate, 10 mM CDTA, 400 mM sodium sulfate, 25 µM APMBT, 15 mM sodium pyrophosphate, 2 µM coelenterazine; pH 5.5). Photon emission was quantified as previously described. The individual and combined chemical formulations summarized in Table 3 were evaluated for their ability to quench Renilla luciferase luminescence by adding 100 µl of the test solution to the luminescent reaction, then quantifying residual light emission as before.

The effect of quenching firefly luciferase luminescence using substrate analogs can be reasonably extended to the luminescent reactions catalyzed by other beetle luciferases. In addition to their common substrate requirements and reaction chemistries, beetle luciferases are of common evolutionary origin, displaying at least 45% protein sequence homology. It is therefore logical that substrate analogs of beetle luciferin, and other chemicals such as those demonstrated in Table 1 to quench one beetle luciferase, will be similarly potent in quenching the luminescent reaction of luciferases purified from any of the many species of luminous beetles. Therefore, general BLQ Reagent include the representative formulations presented in Table 1, as well as any combination of their constituent chemicals such as to affect at least a 1,000-fold diminution of luminescent intensity from beetle luciferase reactions.

Figure 4:
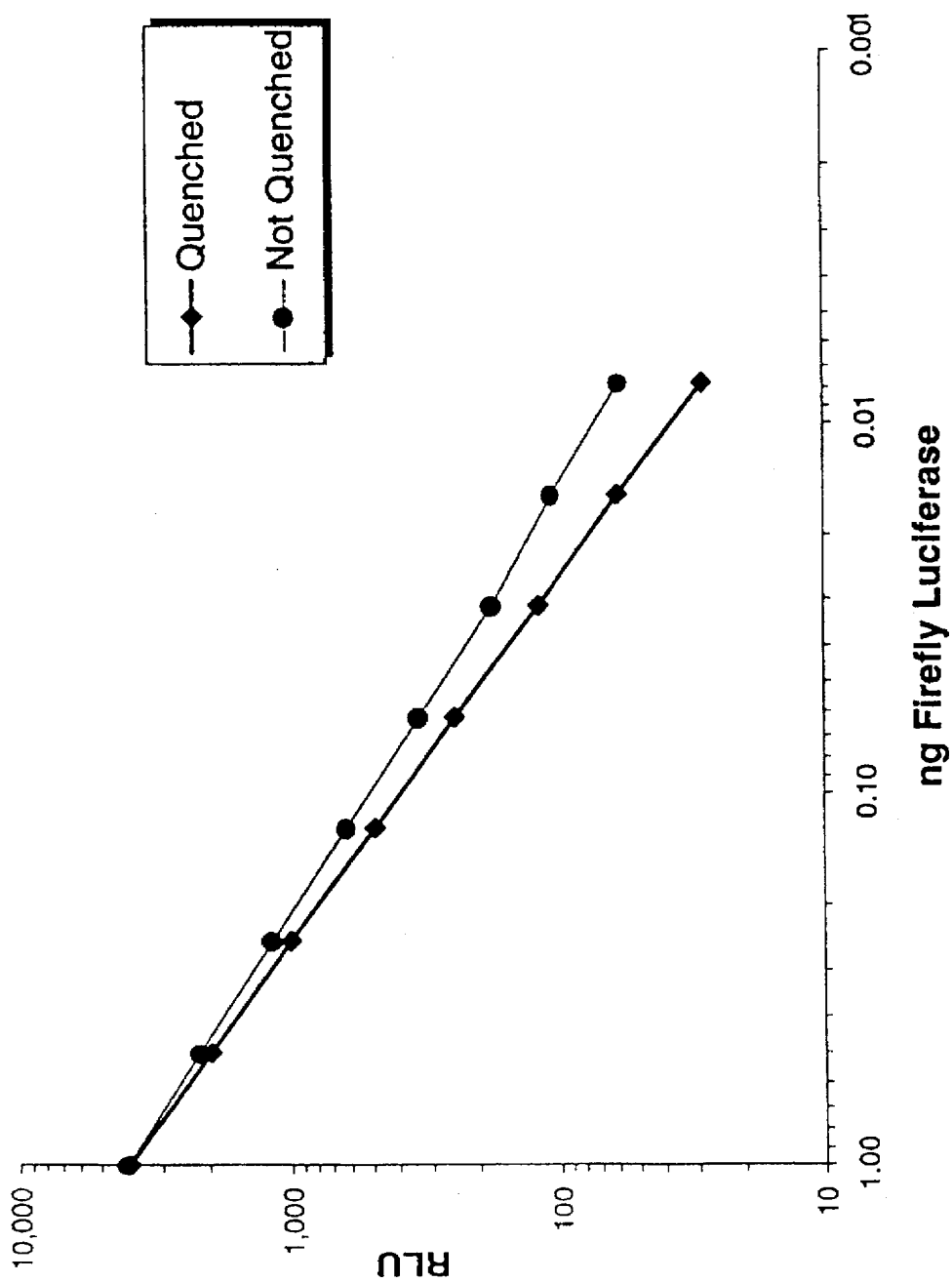
FIG. 4 is a graph showing general quenching of luminescence reactions catalyzed by luciferases from three distinct organisms using quench reagents according to the present invention.

FIG. 4 demonstrates that a reagent capable of quenching the luminescence from the reaction of one beetle luciferase (that of *Photinus pyralis*, the North American firefly) is similarly potent in quenching the luminescent reaction catalyzed by a luciferase of distinct beetle origin (that of *P. plagiophthalamus*, the Jamaican click beetle). *P. plagiophthalamtus*, is the most evolutionarily distant of the luminous beetles to *P. pyralis*, and thus the luciferases of these two beetles are representative of the full range of beetle luciferases. Note that the Y-axis of FIG. 4 is logarithmic. The unquenched firefly assay was performed by adding 20 µl of an extract of mammalian cells expressing firefly luciferase (prepared as described below) into a luminometer tube containing 100 µl Promega Luciferase Assay Reagent. The unquenched click beetle luciferase assay was performed in a similar fashion except the enzyme sample was gained by diluting purified click beetle luciferase to approximately 5 µg/ml in Promega Reporter Lysis Buffer containing 1 mg BSA/ml. Both beetle luciferase reactions were quenched by adding 100 µl BLQ Reagent into the

TABLE 3

Evaluation of Compounds for Their Ability to Quench the Luminescent Reaction of Renilla Luciferase

| Functional Type of Inhibitor | Renilla Luciferase Quench (RLQ) Reagent Tested | Representative Assay Concentration of Compound(s) Tested | Percent (%) Residual Renilla Luciferase Activity |
|---|---|---|---|
| pH Shift | Citric Acid, pH 3 | 6.67 mM | 5.3 |
| General Protein | SDS | 0.33% (w/v) | 0.00029 |
| Denaturants | Tween ®20 | 0.33% (v/v) | 3.4 |
|  | Triton ® X-100 | 0.33% (v/v) | 3.1 |
|  | n-Butanol | 1.67% (v/v) | 4.5 |
| Other | NaI | 330 mM | 5.9 |
| Selected Combined | I$_2$, NaI | .93 mM, 33 mM | 0.000053 |
| Formulations | SDS, NaI | 0.33% (w/v), 170 mM | 0.00067 |
|  | Tween ® 20, NaI | 0.33% (v/v), 170 mM | 0.00081 |
|  | Tween ® 20, n-Butanol, NaI | 0.33% (v/v), 0.83% (v/v), 130 mM | 0.00084 |
|  | Triton ® X-100, NaI | 0.33% (v/v), 170 mM | 0.022 |
|  | Tween ® 20, Citric Acid, pH 3 | 0.33% (v/v), 6 mM | 0.89 |
|  | Tween ® 20, n-Butanol | 0.33% (v/v), 0.83% | 1.4 |
|  | Tween ®20, n-Butanol, Citric Acid, pH 3 | 0.33% (v/v), 0.83% (v/v), 2.67 mM | 1.4 |
| Control Reaction: No Inhibitor Added |  |  | (100%) | luminometer tube immediately following the measurement of the uninhibited control reactions. In this example, BLQ Reagent is comprised of 10 mM HEPES, 50 mM Na$_4$PPi, and 200 mM NaI; pH 6.5. Luminescence from both the control (i.e., 100% equivalent) and quenched beetle luciferase reactions were quantified by integrating light emission over a 10 second period in a Turner Designs luminometer fitted with a 410× neutral density filter.

FIG. 4 also demonstrates that luciferase isolated from the sea pansy (*Renilla reniformis*) can be efficiently quenched by the addition of selected Renilla Luciferase Quench (RLQ) Reagent formulations, as summarized in Table 3. The control luminescent reaction (100% equivalent) was performed by adding 20 µl of purified Renilla luciferase, diluted to 0.3 µg/ml in Mathews' Buffer (0.5M NaCl, 0.1M K$_2$HPO$_4$, 1.0 mM Na$_2$EDTA, 0.02% BSA, pH 7.6; from Mathews, et al., 1977) into 100 µl Mathews' Buffer containing 1 µM benzyl coelenterazine. The Renilla luminescent reaction was subsequently quenched by adding into the luminometer tube 100 µl of RLQ Reagent which, in this example, was composed of 0.66% SDS. Luminescence from both control and quenched Renilla luciferase reactions was quantified using a luminometer, as described previously.

The ability to quench luminescent reactions catalyzed by firefly, click beetle and Renilla luciferases, as shown in FIG. 4, demonstrates that luminescent reactions catalyzed by evolutionarily diverse luciferase enzymes are capable of being efficiently quenched by selected chemical agents.

Reagent formulations for selective quenching of beetle luciferases

Implicit to the concept of an integrated (i.e., sequential-measurement) dual-enzyme reporter assay is the necessity to efficiently quench luminescence from the first reporter enzyme such that the activity of the second luminescent reporter is not inhibited. Therefore a quench reagent is required that is extremely potent in quenching luminescence from the firefly reaction but can exist as a passive component in the subsequent luminesces reaction catalyzed by Renilla luciferase. Selected chemical components of Beetle Luciferase Activation (BLA) Reagent, and chemicals identified in Table 1 as candidate Beetle Luciferase Quench (BLQ) Reagents, were further evaluated to assess any inhibitory interaction they may have with the luminescent reaction catalyzed by Renilla luciferase. Table 4 summarizes the affect of these selected chemicals on the luminescent activity of Renilla luciferase. Because of its potent inhibitory affect on the firefly reaction, sodium pyrophosphate (Na$_4$PPi) was tested first. 100 µl Mathews' Buffer supplemented with 2 µM benzyl-coelenterazine and 15 mM Na$_4$PPi was dispensed into a luminometer tube containing approximately 3 ng of purified Renilla luciferase in 100 µl Mathews' Buffer, and luminescence was quantified. When compared to a control reaction lacking sodium pyrophosphate it is evident that this compound has no inhibitory affect on the luminescent reaction catalyzed by Renilla luciferase. Therefore, all other chemicals were tested in combination with Na$_4$PPi as follows: 100 µl of purified Renilla luciferase, diluted to approximately 0.3 µg per ml in a solution of 75 mM Tricine (pH 8), 500 mM NaCl mM EDTA, was dispensed into luminometer tubes. The luminescent reaction was activated by adding 100 µl of Renilla substrate solution comprised of 15 mM Na$_4$PPi (pH 5.5) and 2 µM benzyl coelenterazine in combination with one of several concentrations of the test reagents presented in Table 4.

TABLE 4

Evaluation of Chemicals Comprising BLA and BLQ Reagent Formulations for their Compatability with the Luminescent Reaction of Renilla Luciferase

| Compound(s) Tested | Representative Assay Concentration of Compound(s) Tested | Percent (%) Renilla Luciferase Activity |
|---|---|---|
| Na$_2$SO$_4$, Na$_4$PPi | 400 mM, 7.5 mM | 187 |
| NaCl, Na$_4$PPi | 400 mM, 7.5 mM | 154 |
| MgSO$_4$, Na$_4$PPi | 2 mM, 7.5 mM | 107 |
| CDTA, Na$_4$PPi | 10 mM, 7.5 mM | 107 |
| CoenzymeA, Na$_4$PPi | 135 uM, 7.5 mM | 107 |
| Na$_4$PPi | 7.5 mM | 102 |
| Methanol, Na$_4$PPi | 2.5% (v/v), 7.5 mM | 101 |
| Luciferin, Na$_4$PPi | 240 µM, 7.5 mM | 100 |
| APMBT, Na$_4$PPi | 12.5 µM, 7.5 mM | 98.5 |
| ATP, Na$_4$PPi | 265 uM, 7.5 mM | 94.9 |
| DTT, Na$_4$PPi | 15 mM, 7.5 mM | 78.5 |
| IFP Ink, Na$_4$PPi | 1/3000x, 7.5 mM | 65.2 |
| iso-Propanol, Na$_4$PPi | 2.5% (v/v), 7.5 mM | 61.7 |
| Dehydroluciferin, Na$_4$PPi | 2.5 mM, 7.5 mM | 49.9 |
| NaI, Na$_4$PPi | 0.4 M, 7.5 mM | 40.0 |

Control Reaction: Mathew's Buffer without added chemicals (100%)

Dual-luciferase reporter assays

In a second embodiment of the present invention, a luminescence assay utilizing two or more distinct enzymes, and a quench reagent specific for only one of the enzymes is described. In the second embodiment, rather than introducing a general quench reagent which quenches all luminescence reactions, a reagent which specifically inhibits only one type of enzyme-mediated luminescence reaction is added to the sample cell. Such quench reagents will be referred to as specific quench reagents; and referred to as quench-and-activate reagents when additionally formulated to also simultaneously initiate a second enzyme-mediated luminescence reaction.

In this assay, a sample containing two distinct enzymes, such as firefly luciferase and Renilla luciferase, or any combination of distinct enzymes, is assayed. First, an activating agent for one of the two enzymes is added into a sample well, and the resulting luminescence measured as described above. A specific quench-and-activate reagent is then added into the well. The reagent specifically quenches the first enzyme-mediated reaction, and simultaneously activates the second enzyme-mediated reaction. Or, alternatively, the specific quench reagent and a second light activating reagent specific for the second enzyme-mediated luminescence reaction can be added to the sample well simultaneously. The luminescence from the second reaction is then measured in the same manner as the first. Optionally, luminescence from the sample may then be completely quenched by adding a general quench reagent to the sample.

In this manner, the present invention affords a multiplex luminescence assay capable of measuring two distinct parameters within a single sample. As noted above, one of the enzyme-mediated reactions can act as an internal standard, while the other of the enzyme-mediated reactions functions as a genetic marker or other experimental variable.

The traditional assay chemistries used to quantify the activity of beetle (Wood, 1991) and Renilla (Mathews, et al., 1977) luciferases are incompatible. The present invention embodies innovative chemical formulations that meld the Renilla luciferase assay with that of the firefly or click beetle luciferase reaction, thus creating a novel dual-luciferase reporter assay. These formulations are here given the generic designations of Beetle Luciferase Activation (BLA) Reagent and Beetle Luciferase Quench & Renilla Luciferase Activation (BLQRLA) Reagent.

BLA Reagent (75 mM HEPES, 4 mM MgSO$_4$, 20 mM DTT, 100 µM EDTA, 530 µM ATP, 270 µM CoA, 470 µM beetle luciferin; pH 8.0) is a derivation of Promega's Luciferase Assay Reagent formulation disclosed in their Technical Bulletin #101 (available film Promega Corp, Madison, Wis.). BLA Reagent is formulated to sustain the luminescent reaction of firefly luciferase and to later complement BLQRLA Reagent in promoting maximal luminescent activity from the Renilla luciferase reaction.

Table 5 presents representative formulations of the various BLQRLA Reagents tested, and summarizes their respective efficiencies in i) selectively quenching luminescence from the firefly luciferase reaction and ii) activating and sustaining maximal Renilla luciferase luminescence. Assays were performed using a cell extract prepared from CHO cells expressing firefly luciferase (described in detail below) and further supplemented with purified Renilla luciferase (approximately 0.3 µg/ml). Thus, the prepared extract simulates the experimental condition in which a single cell population is induced to simultaneously express two distinct luciferase reporter enzymes. Reactions to determine Renilla luciferase activity were conducted by first dispensing 10 µl of extract into a luminometer tube containing 100 µl BLA Reagent (75 mM HEPES, 4 mM MgSO$_4$, 20 mM DTT, 100 µM EDTA, 530 µM ATP, 270 µM CoA, 470 µM beetle luciferin: pH 8.0), then adding 100 µl of one of the various BLQRLA test reagents. BLQRLA Reagents are composed of 7.5 mM acetic acid (pH 5.0) in combination with one of the test mixtures presented in Table 5. The 100% control value for Reporter #1, the firefly luciferase-mediated luminescent reaction, was determined by quantifying light emission from said reaction prior to addition of the designated BLQRLA Reagent. The 100% control value for Reporter #2, the Renilla luciferase-mediated luminescent reaction, was determined using the dual-reporter assay format in which the addition of a reagent that concomitantly activates and sustains the luminescent reaction of Renilla luciferase (Reporter #2). These examples convincingly demonstrate the unique, integrated nature of the dual-luciferase assay. The activity of both luminescent reporter enzymes are rapidly quantified from within the same sample, contained in a single tube, using the same instrument. Note, as in FIG. 4, the Y-axis in FIGS. 5 and 6 is logarithmic.

Figure 5:
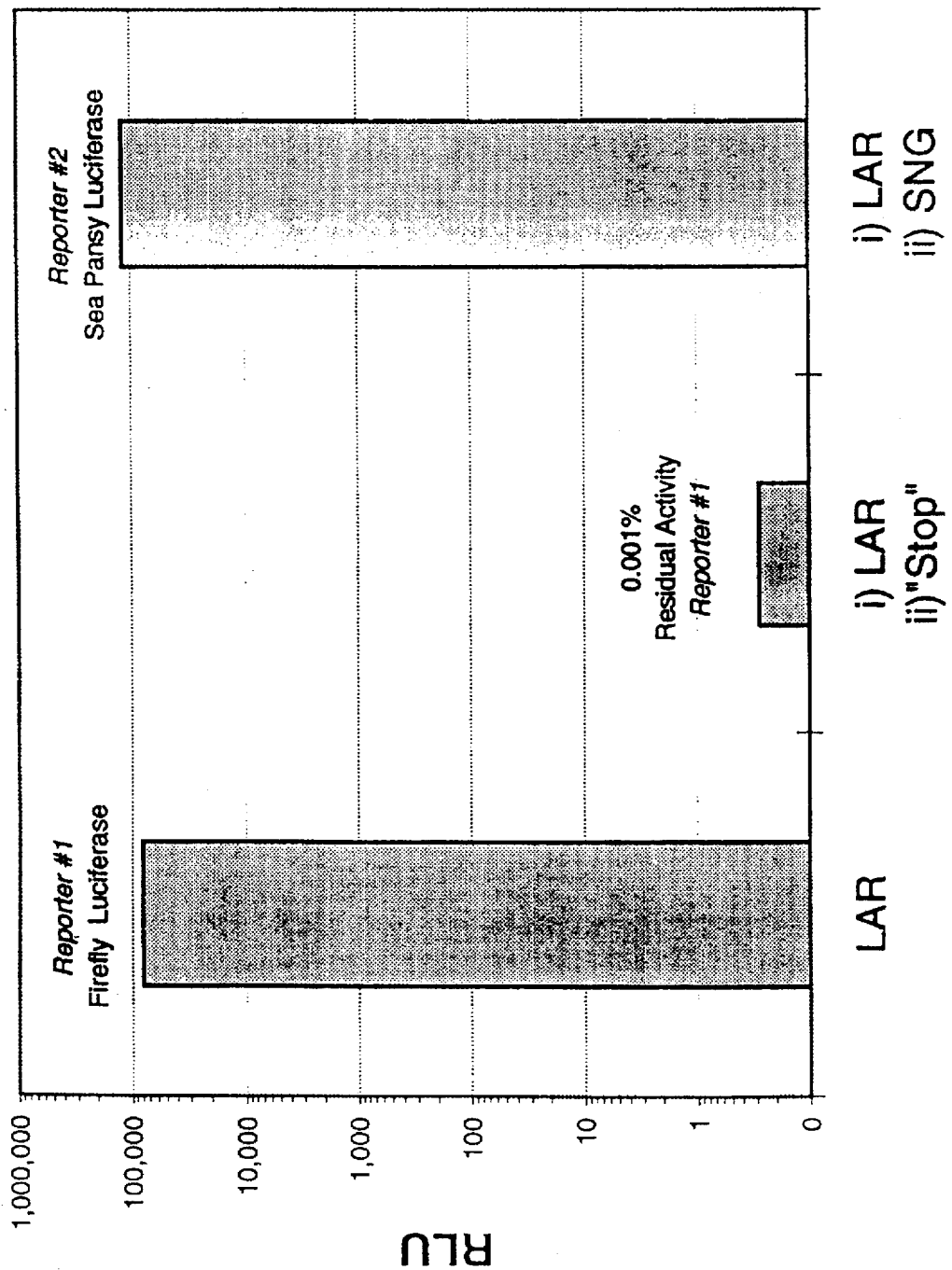
FIG. 5 shows the results of a dual-luciferase reporter assay according to the present invention utilizing firefly luciferase as the first reporter, and Renilla (sea pansy) luciferase as the second reporter.
Figure 6:
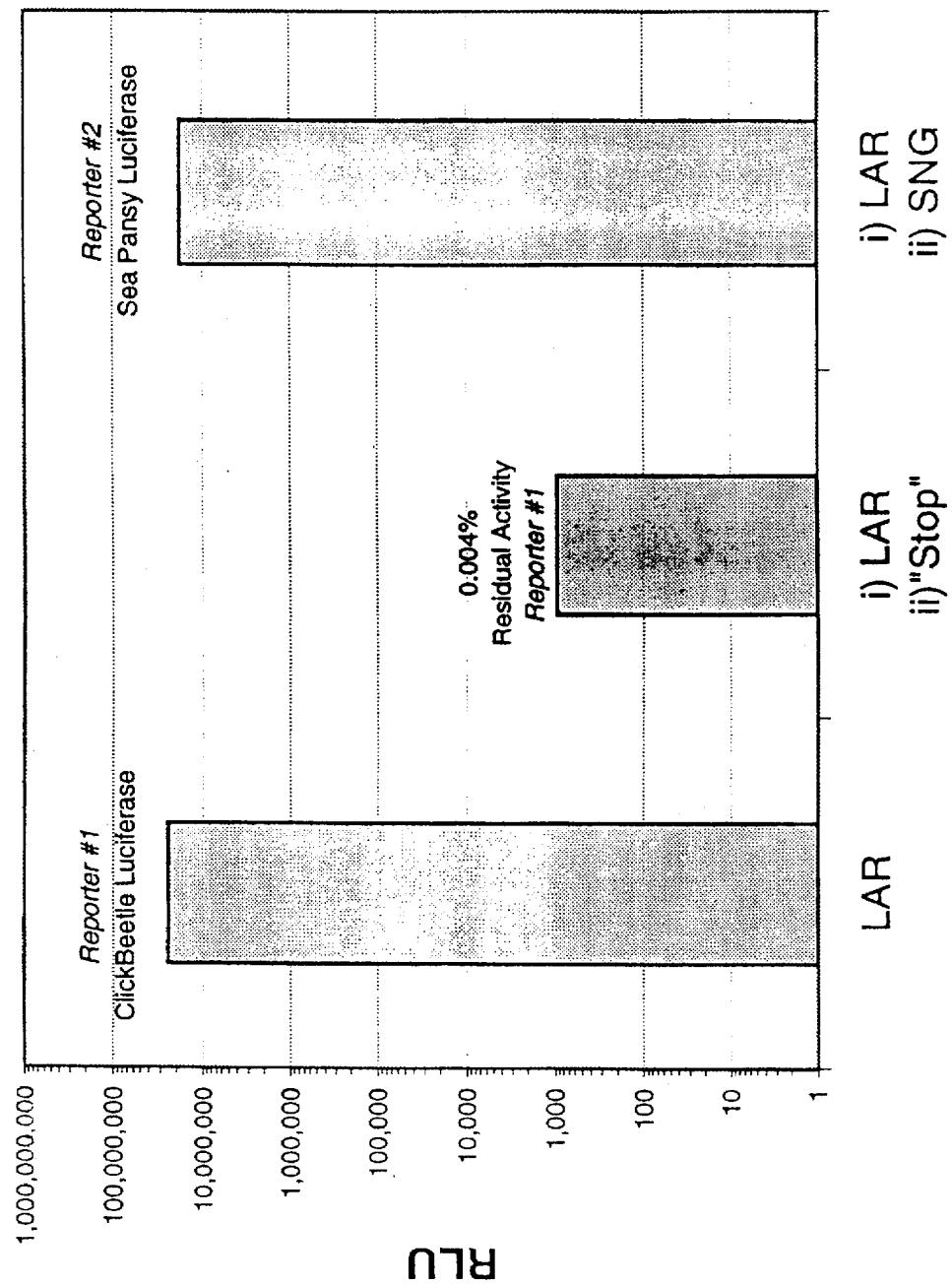
FIG. 6 shows the results of a dual-luciferase reporter assay according to the present invention utilizing click beetle luciferase as the first reporter, and Renilla luciferase as the second reporter.

FIG. 5 presents the measured activity (in terms of relative light units; RLU) of firefly and Renilla luciferases using the dual-luciferase reporter format of the invention. The luminescent activities of the two mixed luciferases were measured sequentially frown the same sample tube, using the same instrument. A cell-free extract expressing firefly luciferase was prepared, as described below, and further supplemented with purified Renilla at a concentration of approximately 0.3 ng/ml. The activity of Reporter #1, firefly luciferase, was measured by adding 20 µl of the cellular extract to 100 µl of BLA Reagent. Firefly luminescence was quantified by integrating light emission over a 10 second period using a Turner Designs luminometer whose sample chamber was fitted with a 410× neutral density filter. The activity of Reporter #2, Renilla luciferase, was determined from the same sample by injecting 100 µl of BLQRLA reagent into the same luminometer tube. For the purpose of FIGS. 5 and 6, BLQRLA reagent is comprised of 15 mM Na$_4$PPi, 7.5 mM sodium acetate, 10 mM CDTA, 400 mM Na$_2$SO$_4$, 25 µM APMBT, 1% methanol, 2 µM benzyl-coelenterazine; pH 5.0. Luminescent intensity of the Renilla catalyzed reaction was quantified immediately after addition of BLQRLA Reagent, without the need for adjustments to the luminometer.

Residual luminescence from the quenched firefly luciferase reaction was determined independently to assess the luminescent background its reaction contributed to the

TABLE 5

Evaluation of Beetle Luciferase Quench & Renilla Luciferase Activation (BLQRLA) Reagents

| BLQRLA Test Reagents (and Associated BLQ Reagents) | Assay Concentration | Percent (%) Residual Firefly Luciferase Activity | Percent (%) Renilla Luciferase Activity |
|---|---|---|---|
| Na$_4$PPi | 7.5 mM | 1.0 | — |
| Na$_4$PPi + Coelenterazine | 7.5 mM, 1 µm | — | 65.83 |
| Na$_4$PPi, APMBT | 7.5 mM, 12.5 µm | 0.001 | — |
| Na$_4$PPi, APMBT, + Coelenterazine | 7.5 mM, 12.5 µm, 1 µM | — | 53.1 |
| Na$_4$PPi, CDTA | 7.5 mM, 10 mM | 0.13 | — |
| Na$_4$PPi, CDTA, + Coelenterazine | 7.5 mM, 10 mM, 1 µM | — | 64.66 |
| Na$_4$PPi, CDTA, APMBT | 7.5 mM, 5.0 mM, 12.5 µM | 0.0002 | — |
| Na$_4$PPi, CDTA, APMBT, + Coelenterazine | 7.5 mM, 5.0 mM, 12.5 µM, 1 µM | — | 58.5 |
| Na$_4$PPi, APMBT, Na$_2$SO$_4$ | 7.5 mM, 12.5 µM, 200 mM | 0.00075 | — |
| Na$_4$PPi, APMBT, Na$_2$SO$_4$, + Coelenterazine | 7.5 mM, 12.5 µM, 200 mM, 1 µM | — | 92.36 |
| Na$_4$PPI, CDTA, Na$_2$SO$_4$ | 7.5 mM, 10 mM, 200 mM | 0.048 | — |
| Na$_4$PPI, CDTA, Na$_2$SO$_4$, + Coelenterazine | 7.5 mM, 10 mM, 200 mM, 1 µM | — | 100.52 |
| Na$_4$PPI, CDTA, APMBT, Na$_2$SO$_4$ | 7.5 mM, 5.0 mM, 12.5 µM, 200 mM | 0.0001 | — |
| Na$_4$PPi, CDTA, APMBT, Na$_2$SO$_4$, + Coelenterazine | 7.5 mM, 5.0 mM, 12.5 µM, 200 mM, 1 µM | — | 90.4 |
| Na$_4$PPi, Na$_2$SO$_4$ | 7.5 mM, 200 mM | 0.23 | — |
| Na$_4$PPi, Na$_2$SO$_4$, + Coelenterazine | 7.5 mM, 200 mM, 1 µM | — | 100 |
| Control Reaction #1: BLA Reagent Only | | (100%) | — |
| Control Reaction #2; BLQRLA reagent consisting of (3.75 mM HAc, 7.5 mM Na$_4$PPI, 200 mM Na$_2$SO$_4$, 1 µM Coelenterazine; pH 5.0) | | — | (100%) | control BLQRLA Reagent (7.5 mM acetic acid, 15 mM Na$_4$PPi, 400 mM Na$_2$SO$_4$, 2 µM coelenterazine; pH 5.0) was added to the firefly luciferase reaction in a 1:1 volume ratio.

FIGS. 5 and 6 demonstrate the invention applied to the situation in which different beetle luciferase reactions (Reporter #1 ) are quantified then selectively quenched by measured activity value of the Renilla luciferase reaction. A reagent was prepared that is similar in all respects to the formulation of BLQRLA Reagent except that it does not contain coelenterazine. As before, this formulation is designated "Beetle Luciferase Quench (BLQ) Reagent". The luminescent reaction catalyzed by firefly luciferase was activated, as before, by adding 20 μl of prepared lysate to 100 μl BLA Reagent. 100 μl of BLQ Reagent was then immediately injected into the sample tube and residual firefly luciferase luminescence was measured. Less than 0.0004% residual luminescent activity was determined to persist following quenching of the firefly luciferase reaction. Therefore, in this example, approximately 0.0004% of the luminescent signal measured from the second luciferase reporter enzyme reaction is contributed as signal interference from the first luciferase reporter enzyme.

FIG. 6 presents the measured activity (in terms of RLU) of Jamaican click beetle and Renilla luciferases using the dual-luciferase reporter format of the invention. The luminescent activities of the two mixed luciferases were measured sequentially from the same sample tube, using the same instrument. Purified click beetle and Renilla luciferases were diluted to approximately 5 μg/ml each in Promega's Reporter Lysis Buffer containing 0.5 mg BSA/ ml. 20 μl of the enzyme mixture was added to 100 μl BLA contained in a luminometer tube, and the luminescence signal from Reporter #1 (click beetle luciterase) was measured by integrating light emission over a 10 second period using a Turner Designs luminometer fitted with a 410× neutral density filter. The activity of Reporter #2, Renilla luciferase, was determined from the same sample by injecting 100 μl of BLQRLA reagent into the same luminometer tube. The formulation of BLQRLA Reagent was the same as described above for quenching firefly luminescence and concomitantly activating the Renilla luciferase reaction.

Residual luminescence from the quenched click beetle reaction was determined independently to assess the percentage of background signal its reaction contributed to the value measured for the Renilla luciferase reaction. The method of determination, and the formulation of BLQ Reagent, were the same as those described above for the firefly/Renilla dual-luciferase reporter assay. In this example, less than 0.004% of the luminescence value determined for the Renilla luciferase reaction is contributed as signal interference from the preceding click beetle luciferase reaction.

In summary, the integrated chemistry of the dual-luciferase assay provides the capability of discriminating the individual luminescent signals from the reaction of two dissimilar luciferase reporter enzymes expressed within a single sample. An illustrative outline of the dual-luciferase assay, which typically requires less than 35 seconds to complete, is as follows:

1. Place tube containing prepared cell extract in luminometer
2. Add BLA Reagent to sample tube
3. Quantify beetle luciferase activity (Reporter #1: experimental value)
4. Add BLQRLA Reagent to the same sample tube
5. Quantify Renilla luciferase activity (Reporter #2: internal control value).

This outline is for illustrative purposes only, and does not limit the scope of the present invention in any fashion.

Cell culture manipulations and lysate preparation

The preceding tables, and some of the following examples, involve the use of extracts prepared from cultured mammalian cells transiently expressing firefly luciferase. In all cases, Chinese hamster ovary (CHO) cells were cultured in 75 cm$^2$ polystyrene culture flasks containing 25 ml of DMEM+FBS medium (Dulbecco's Modified Eagles Medium supplemented with 10% fetal bovine serum). Culture flasks were incubated in a 37° C., 5% $CO_2$ environment until approximately 90% confluence was observed. Growth medium was removed and cells were overlayered with 5 ml of Hank's Balanced Salts solution supplemented with a 1:10 dilution of commercially prepared Trypsin-EDTA solution. The trypsin solution was aspirated 30 seconds after addition and cells were allowed to incubate for 2 minutes at 37° C. Cells were harvested by rinsing the culture flask with a 10 ml volume of DMEM+FBS medium. Cell liter was determined and 2.0×10$^6$ cells were transferred to a 50 ml, sterile, screw-cap tube containing sufficient DMEM+FBS to obtain a final cell suspension volume of 16.5 ml. In separate preparations, 900 μl of 250 mM $CaCl_2$ containing 10 μg of the firefly luciferase expression plasmid pGL3-Control (Promega Corp., Madison, Wis.), were added to 900 μl of 2× HEPES buffer. The resulting 1.8 ml volume of colloidal DNA/calcium phosphate was added to the prepared 16.5 ml volumes of cell suspension. The combined suspension was rapidly mixed and 6 ml aliquots were immediately dispensed into each of three 100 cm$^2$ round polystyrene culture plates. Each plate contained the equivalent of 6.7×10$^5$ cells and 3.3 μg of plasmid DNAs encoding firefly luciferase. Treated cells were incubated in a 37° C./5% $CO_2$ environment for 30 hours.

Extracts were prepared by aspirating the growth medium, washing adherent cells once with 10 ml phosphate buffered saline (PBS; 137 mM NaCl, 2.68 mM KCl, 1.47 mM $KH_2PO_4$, 8.1 mM $Na_2HPO_4$; pH 7.4), adding 400 μl of Promega's Reporter Lysis Buffer and scraping vigorously with a plastic cell lifter. Crude lysates were transferred to 1.5 ml microfuge tubes and cleared of cellular debris by spinning at 14,000 rpm in a refrigerated microfuge.

All cell culture-grade medium components, 10× Trypsin-EDTA, and salt solutions were obtained from GibcoBRL (Gaithersburg, Md.). All plasticware was obtained from Corning (Corning, N.Y.). $CaCl_2$ and HEPES buffer solutions are components of the Profection® Mammalian Transfection System which, along with Reporter Lysis Buffer, are commercially available from Promega Corp. (Madison, Wis.).

EXAMPLES

Example 1

Cumulative Signal Interference due to Light Refraction from Multiple Luminescent Samples in Distant Wells of Clear Plastic Microplates, and the Elimination of Light Refraction by Post-Read Quenching of Luminescent Reactions FIG. 3-A is a plot of the RLU values measured from each well of a 96-well clear plastic plate containing only 32 samples of varying luminescent intensity. It demonstrates the general phenomenon, and cumulative affect, of signal cross-talk between multiple luminescent samples in distant wells of a clear plastic micro-well plate.

A prepared lysate of CHO cells transfected with pGL3-Control was dispensed into each of the eight wells of alternating sample columns of a clear 96-well plate, as described for FIG. 2. As before, the plate was loaded into a plate-reading luminometer programmed to sequentially inject Promega Luciferase Assay Reagent and measure luminescence from each of the 96-wells. An unacceptably high percentage of refracted and scattered light is measured as signal interference in the columns of empty wells (i.e., columns 3, 4, 6, 7, 9, 10 and 12) that are adjacent to columns with actively luminescent reactions. In this example, there is no signal interference measured in the empty sample wells of column 1 because they are injected with Promega Luciferase Assay Reagent and measured for luminescent activity before the first luminescent reaction (well A2) is initiated.

FIG. 3-B is a plot of RLU values measured from each well of a 96-well clear plastic plate prepared and processed similar to that described in FIG. 3-A, but the luminometer was programmed to further inject 100 μl of Beetle Luciferase Quench (BLQ) reagent immediately following sample measurement. BLQ reagent was derived from formulations presented in Table 1 and, in this example, consisted of 10 mM HEPES, 50 mM Na$_4$PPi, 200 mM NaI; pH 6.5. FIG. 3-B convincingly demonstrates that post-read quenching of luminescent reactions contained in clear multi-well plates effectively eliminates signal interference by suppressing light cross-talk from preceding samples.

Example 2

Impact on the accurate measurement of light signal from unquenched luminescent samples in clear multiwell plates Table 2 shows the percent error determined for light signal measured from sets of luminescent samples contained in clear multi-well plates when a general quench reagent is not utilized to extinguish previous luminescent reactions. Average luminescent signal was determined for the four samples in each row of the unquenched multi-well plate presented in FIG. 3-A, then compared to the values determined for the respective sample sets contained in the quenched multi-well plate of FIG. 3-B. It is seen that signal interference from unquenched reactions contributes less than 2% to the total light signal measured from samples in row A (an average luminescent value of 4,000 RLU) but contributes greater than 100% to the average signal measured from samples in row H (average luminescent value of 100 RLU). Thus, the adverse affects of cumulative light cross-talk between sample wells have much greater impact when measuring signals from luminous samples with low activity as opposed to samples with high luminescent activity. Indeed, extreme background signal resulting from cumulative light cross-talk in clear multi-well plates makes the accurate measurement of low-light samples impossible and, in the absence of a suitable luminescence quench reagent, precludes the use of the more desirable clear plastic multi-well plates for luminometric analysis.

Example 3

Reagents for the rapid, general quenching of luminescent reactions catalyzed by luciferases from three species of luminous organisms FIG. 4 presents the percent residual luminescent activity measured after the addition of selected quench reagents to the luminescent reactions catalyzed by three distinct luciferases. Formulations Beetle Luciferase Quench (BLQ) and Renilla Luciferase Quench (RLQ) Reagents derived from Tables 1 and 3 were used to quench the luminescent activity of luciferases purified from two terrestrial organisms, the North American firefly (*Photinus pyralis*) and Jamaican click beetle (*Pyrophorus plagiophthalamus*), and a marine organism, the sea pansy (*Renilla reniformis*).

Click beetle and firefly luciferase reactions were performed using Luciferase Assay Reagent and Reporter Lysis Buffer provided as components of Promega's Luciferase Assay System kit (Promega Corp., product # E4030) as previously described. The formulation of BLQ Reagent used in this example to quench the luminescence reactions catalyzed by firefly and click beetle luciferases is 10 mM HEPES, 50 mM Na$_4$PPi, and 200 mM NaI; pH 6.5. Quantification of the Renilla luciferase luminescent reaction was performed as described earlier, and was subsequently quenched by adding an equal volume of an RLQ Reagent comprised of 0.66% SDS. Quantification of both the control (100% equivalent) luminescent reactions and quenched reactions for each of the three luciferases tested was performed using a Turner Designs luminometer, as described in previous sections.

Example 4

Integrated dual-luciferase reporter assay

Sequential measurement of firefly luciferase and Renilla luciferase luminescent reactions FIG. 5 presents the activity (RLU) of firefly and Renilla luciferases measured using the integrated dual-reporter format of the invention. The luminescent activities of the two mixed luciferases were measured sequentially from the same sample tube, using the same instrument.

CHO cells transfected with pGL3-Control DNA, and therefore expressing firefly luciferase, were prepared and further supplemented with purified Renilla luciferase, as described previously. The activity of Reporter #1, firefly luciferase, was measured by adding 20 μl of the prepared extract to 100 μl Beetle Luciferase Activation (BLA) reagent. Luminescent intensity was quantified by integrating light emission over a 10 second period using a Turner Designs luminometer fitted with a 410× neutral density filter. The activity of Reporter #2, Renilla luciferase, was determined from the same sample by injecting 100 μl Beetle Luciferase Quench & Renilla Luciferase Activation (BLQRLA) Reagent into the same luminometer tube. Luminescent intensity of the Renilla luciferase reaction was quantified in the same way as that of the firefly reaction, without the need for adjustments to the luminometer. Typically, the format of the invention requires less than 35 seconds to measure the luminescent activity of both luciferase reporter enzymes.

Residual luminescence from the quenched Reporter #1 reaction was measured to determine the extent of signal interference contributed to the activity value determined for Reporter #2. The luminescent reaction of firefly luciferase was activated, as before, then 100 μl of BLQ Reagent was immediately injected into the sample tube and residual firefly luciferase activity was measured. Less than 0.0004% residual luminescent activity was determined to persist following quenching of the firefly luciferase reaction.

A detailed description of BLA, BLQRLA and BLQ Reagent formulations are described in preceding sections.

Example 5

Integrated dual-luciferase reporter assay

Sequential measurement of click beetle luciferase and Renilla luciferase luminescent reactions FIG. 6 presents the activity (RLU) of click beetle and Renilla luciferases measured using the integrated dual-reporter format of the invention. Measurements of Reporter #1 (click beetle luciferase) and Reporter #2 (Renilla luciferase) luminescent activities, as well as the determination of residual luminescence from Reporter #1, were conducted as described in Example 4. In this example, less than 0.004% residual luminescent activity was determined to persist following quenching of the click beetle luciferase reaction.

It is understood that the present invention is not limited to the particular reagent formulations, steps, or methods disclosed herein, but rather encompasses all such forms thereof as come within the scope of the attached claims.

BIBLIOGRAPHY

Blaise, C., et al. (1994) BioTechniques: 16, 932–937.

Bronstein, et al. (1991) Bioluminescence and Chemiluminescence: Current Status. (eds. P. E. Stanley and L. J. Kricka) John Wiley & Sons, Inc. pp. 73–82.

Bronstein, I., et al. (1994) Anal-Biochem.: 219, 169–181.

Denburg, et al. (1969) Archives of Biochemistry and Biophysics: 134, 381–394.

Denburg, J. L., and McElroy, W. D. (1970) Archives of Biochemistry and Biophysics: 141,668–675.

Flanagan, W. M. et al. (1991) J. Virology: 65, 769–786.

Jain, V. K. and Magrath, I. T. (1992) BioTechniques: 12, 681–683.

Kobatake, et al. (1993) Bioluminescence and Chemiluminescence (ed. A. A. Szalay, et al.) John Wiley & Sons, Chichester, pp. 337–341.

Kondepudi, T., et al., Poster abstract #725, presented at annual meeting of the American Society of Cell Biologist, Dec. 10–14, 1994, San Francisco, Calif.

Leckie, F. et al. (1994) BioTechniques: 17, 52–57.

Lee, et al. 1970) Archives of Biochemistry and Biophysics: 141, 38–52.

Mathews, J. C. et al. (1977) Biochemistry: 16, 85–91.

Schaap, et. al. (1989) Clinical Chemistry: 35, 1863–1864.

Schram, (1991) Bioluminescence and Chemiluminescence: Current Status. (eds. P. E. Stanley and L. J. Kricka) John Wiley & Sons, Inc., pp. 407–412.

Thompson, J. F., et al. (1991) Gene: 103, 171–177.

Thorp, et al. (1986) Methods in Enzymology: 133, 331–353.

Ward (1985) Chemi- and Bioluminescence (ed. John Burr) Marcel Dekker, Inc., New York, pp. 321–358.

Wood (1995) Curr. Op. Biotech.: 6, 50–58.

Wood, K.(1991) in Bioluminescence & Chemiluminescence: Current Status. (eds. Stanley, P. E., and Kricka, J.) John Wiley & Sons, Chichester. pp. 543–546.

What is claimed is:

1. A method of assaying enzyme-mediated luminescence reactions comprising:
   (a) initiating at least one enzyme-mediated luminescence reaction; then
   (b) quantifying luminescence energy produced by the luminescence reaction; and then
   (c) quenching photon emission from the enzyme-mediated luminescence reaction by introducing at least one quench reagent to the luminescence reaction.

2. The method according to claim 1, wherein in step (a), at least one luciferase-mediated luminescence reaction is initiated.

3. The method according to claim 2, wherein in step (c), the luciferase-mediated reaction is quenched with a quench reagent capable of reducing photon emissions from said luciferase-mediated luminescence reaction by a factor of at least 1,000-fold.

4. The method according to claim 3, wherein in step (c), the luciferase-mediated reaction is quenched with one or more quench reagents selected from the group consisting of
iodide,
iodine,
sulfate,
nitrate,
iso-propanol,
2-(4-aminophenyl)-6-methylbenzothiazole,
dimethyldecylphosphine oxide,
pyrophosphate,
benzothiazole,
2-phenylbenzothiazole,
n-butanol,
trans-1,2,-diaminocyclohexane-N,N,N',N'-tetraacetic acid,
2-(6'-hydroxy-2'-benzothiazolyl)-thiazole-4-carboxylic acid,
ethylenediaminetetraacetic acid,
2(o-hydroxyphenyl)benzothiazole,
India fountain pen ink,
adenosine 5'-triphosphate 2',3'-acyclic dialcohol, periodate oxidized, borohydride reduced,
sodium dodecyl sulfate,
citric acid,
Tween®20,
Triton®X-100,
and mixtures thereof.

5. The method according to claim 3, wherein in step (c), the luciferase-mediated reaction is quenched with at least one composition comprising quench reagents selected from the group consisting of
SDS and NaI;
$I_2$ and NaI;
$Na_4PPi$ and NaI;
$Na_4PPi$, CDTA, and APMBT;
$Na_4PPi$, APMBT, and $Na_2SO_4$;
$Na_4PPi$, CDTA, APMBT, and $Na_2SO_4$;
$Na_4PPi$ and APMBT;
$Na_4PPi$ and iso-propanol;
IFP Ink and APMBT;
APMBT and CDTA;
IFP Ink and CDTA;
IFP Ink and $Na_4PPi$;
SDS and NaI;
Tween®20 and NaI;
Tween®20, NaI, and n-butanol;
Triton®X-100 and NaI;
and mixtures thereof.

6. The method according to claim 3, wherein in step (c), the luciferase-mediated reaction is quenched in a time period not greater than 10 seconds.

7. The method according to claim 2, wherein in step (a), a luciferase-mediated luminescence reaction mediated by a luciferase selected from the group consisting of beetle luciferases and functional equivalents thereof is initiated.

8. The method according to claim 7, wherein in step (a), a luciferase-mediated luminescence reaction mediated by *Photinus pyralis* (North American firefly) luciferase or a functional equivalent thereof is initiated.

9. The method according to claim 8, wherein in step (c), the *Photinus pyralis* luciferase-mediated reaction is quenched with one or more quench reagents selected from the group consisting of
iodide,
iodine,
sulfate,
nitrate,
iso-propanol,
2-(4-aminophenyl)-6-methylbenzothiazole,
dimethyldecylphosphine oxide,
pyrophosphate,
benzothiazole,
2-phenylbenzothiazole,
sodium dodecyl sulfate,
trans-1,2,-diaminocyclohexane-N,N,N',N'-tetraacetic acid,
2-(6'-hydroxy-2'-benzothiazolyl)-thiazole-4-carboxylic acid, ethylenediaminetetraacetic acid,
2(o-hydroxyphenyl)benzothiazole,
India fountain pen ink,
adenosine 5'-triphosphate 2',3'-acyclic dialcohol, periodate oxidized, borohydride reduced,
and mixtures thereof.

10. The method according to claim 9, wherein in step (c), the *Photinus pyralis* luciferase-mediated reaction is quenched by a factor of at least 1,000-fold.

11. The method according to claim 8, wherein in step (c), the *Photinus pyralis* luciferase-mediated reaction is quenched with at least one composition comprising quench reagents selected from the group consisting of
$I_2$ and NaI;
$Na_4PPi$ and NaI;
$Na_4PPi$, CDTA, and APMBT;
$Na_4PPi$, APMBT, and $Na_2SO_4$;
$Na_4PPi$, CDTA, APMBT, and $Na_2SO_4$;
$Na_4PPi$ and APMBT;
$Na_4PPi$ and iso-propanol;
IFP Ink and APMBT;
APMBT and CDTA;
IFP Ink and CDTA;
IFP Ink and EDTA;
IFP Ink, and $Na_4PPi$;
and mixtures thereof.

12. The method according to claim 11, wherein in step (c), the *Photinus pyralis* luciferase-mediated reaction is quenched with at least one composition comprising quench reagents selected from the group consisting of $Na_4PPi$ and NaI; and $Na_4PPi$, CDTA, APMBT, and $Na_2SO_4$.

13. The method according to claim 11, wherein in step (c), the *Photinus pyralis* luciferase-mediated reaction is quenched by a factor of at least 1,000-fold.

14. The method according to claim 7, wherein in step (a), a luciferase-mediated luminescence reaction mediated by *Pyrophorus plagiophthalamus* (Jamaican click beetle) luciferase is initiated.

15. The method according to claim 14 wherein in step (c), the *pyrophorus plagiophthalamus* luciferase-mediated reaction is quenched with one or more quench reagents selected from the group consisting of
iodide,
iodine,
sulfate,
nitrate,
iso-propanol,
2-(4-aminophenyl)-6-methylbenzothiazole,
dimethyldecylphosphine oxide,
pyrophosphate,
benzothiazole,
2-phenylbenzothiazole,
sodium dodecyl sulfate,
trans-1,2,-diaminocyclohexane-N,N,N',N'-tetraacetic acid,
2-(6'-hydroxy-2'-benzothiazolyl)-thiazole-4-carboxylic acid,
ethylenediaminetetraacetic acid,
2(o-hydroxyphenyl)benzothiazole,
India fountain pen ink,
adenosine 5'-triphosphate 2',3'-acyclic dialcohol, periodate oxidized, borohydride reduced,
adenosine triphosphate,
and mixtures thereof.

16. The method according to claim 15, wherein in step (c), *pyrophorus plagiophthalamus* luciferase-mediated reaction is quenched by a factor of at least 1,000-fold.

17. The method according to claim 14, wherein in step (c), the *Pyrophorus plagiophthalamus* luciferase-mediated reaction is quenched with at least one composition comprising quench reagents selected from the group consisting of
$I_2$ and NaI;
$Na_4PPi$ and NaI;
$Na_4PPi$, CDTA, and APMBT;
$Na_4PPi$, APMBT, and $Na_2SO_4$;
$Na_4PPi$, C. DTA, APMBT, and $Na_2SO_4$;
$Na_4PPi$ and APMBT;
$Na_4PPi$ and iso-propanol;
IFP Ink, and APMBT;
APMBT and CDTA;
IFP Ink and CDTA;
IFP Ink and EDTA;
Ink and $Na_4PPi$;
and mixtures thereof.

18. The method according to claim 17, wherein in step (c), the *Pyrophorus plagiophthalamus* luciferase-mediated reaction is quenched by a factor of at least 1,000-fold.

19. The method according to claim 2, wherein in step (a), a luciferase-mediated luminescence reaction mediated by a luciferase selected from the group consisting of anthozoan luciferases and functional equivalents thereof is initiated.

20. The method according to claim 19, wherein in step (a), a luciferase-mediated luminescence reaction mediated by *Renilla reniformis* (sea pansy) luciferase or a functional equivalent thereof is initiated.

21. The method according to claim 20, wherein in step (c), the *Renilla reniformis* luciferase-mediated reaction is quenched with one or more quench reagents selected from the group consisting of
iodide,
iodine,
sodium dodecyl sulfate,
citric acid,
Tween®b 20,
Triton®X-100,
n-butanol,
and mixtures thereof.

22. The method according to claim 21, wherein in step (c), the *Renilla reniformis* luciferase-mediated reaction is quenched by a factor of at least 1,000-fold.

23. The method according to claim 20, wherein in step (c), the *Renilla reniformis* luciferase-mediated reaction is quenched with at least one composition comprising quench reagents selected from the group consisting of
SDS;
SDS and NaI;
$I_2$ and NaI
Tween®20 and NaI;
Tween®20, NaI, and n-butanol;
Triton®X-100 and NaI;
and mixtures thereof.

24. The method according to claim 23, wherein in step (c), the *Renilla reniformis* luciferase-mediated reaction is quenched with a composition comprising SDS; and SDS and NaI.

25. The method according to claim 23, wherein in step (c), the *Renilla reniformis* luciferase-mediated reaction is quenched by a factor of at least 1,000-fold.

26. The method according to claim 1, wherein in step (a) a first enzyme-mediated luminescent reaction mediated by a first enzyme is initiated, and further comprising:
  in step (c), introducing a quench-and-activate composition capable of selectively quenching the first enzyme-mediated luminescence reaction and simultaneously initiating a second enzyme-mediated luminescence reaction distinct from the first enzyme-mediated luminescence reaction; and (d) quantifying luminescence energy produced by the second enzyme-mediated luminescence reaction.

27. The method according to claim 26, wherein in step (a), a first luciferase-mediated luminescence reaction is initiated by a first luciferase.

28. The method according to claim 27, wherein
in step (a), a first luciferase-mediated luminescence reaction mediated by a first luciferase is initiated; and
in step (c) a second and distinct luciferase-mediated luminescence reaction, mediated by a second and distinct luciferase is initiated.

29. The method according to claim 28, wherein in step (c), a quench-and-activate composition capable of reducing photon emissions from the first luciferase-mediated luminescence reaction by a factor of at least 1,000-fold.

30. The method according to claim 28, wherein in step (a), a first luciferase-mediated luminescence reaction mediated by a luciferase selected from the group consisting of beetle luciferases and functional equivalents thereof is initiated; and
in step (c), a second luciferase-mediated luminescence reaction mediated by a luciferase selected from the group consisting of anthozoan luciferases and functional equivalents thereof is initiated.

31. The method according to claim 30, wherein in step (c), the first luciferase-mediated reaction is quenched, and the second luciferase-mediated reaction is initiated with a quench-and-activate composition comprising one or more quench reagents selected from the group consisting of
iodide,
iodine,
sulfate,
nitrate,
iso-propanol,
2-(4-aminophenyl)-6-methylbenzothiazole,
dimethyldecylphosphine oxide,
pyrophosphate,
benzothiazole,
2-phenylbenzothiazole,
trans-1,2,-diaminocyclohexane-N,N,N',N'-tetraacetic acid,
2-(6'-hydroxy-2'-benzothiazolyl)-thiazole-4-carboxylic acid,
ethylenediaminetetraacetic acid,
2(o-hydroxyphenyl)benzothiazole,
India fountain pen ink,
adenosine 5'-triphosphate 2',3'-acyclic dialcohol, periodate oxidized, borohydride reduced,
sodium dodecyl sulfate,
Tween®20,
Triton®X-100,
and mixtures thereof; and
one or more initiating reagents selected from the group consisting of coelenterate luciferins and functional equivalents thereof, and mixtures thereof.

32. The method according to claim 31, wherein in step (c), the first luciferase-mediated reaction is quenched with a quench-and-activate composition capable of reducing photon emissions from the first luciferase-mediated luminescence reaction by a factor of at least 1,000-fold.

33. The method according to claim 26, wherein in step (a), a first enzyme-mediated luminescence reaction mediated by a first *Photinus pyralis* luciferase is initiated.

34. The method according to claim 26, wherein in step (c), a second enzyme-mediated luminescence reaction mediated by a second *Photinus pyralis* luciferase is initiated.

35. The method according to claim 26, wherein in step (a), a first enzyme-mediated luminescence reaction mediated by a first *Renilla reniformis* luciferase is initiated.

36. The method according to claim 26, wherein in step (c), a second enzyme-mediated luminescence reaction mediated by a second *Renilla reniformis* luciferase is initiated.

37. The method according to claim 26, wherein in step (a), a first enzyme-mediated luminescence reaction mediated by a first *Pyrophorus plagiophthalamus* luciferase is initiated.

38. The method according to claim 26, wherein in step (c), a second enzyme-mediated luminescence reaction mediated by a second *Pyrophorus plagiophthalamus* luciferase is initiated.

39. The method according to claim 26, wherein in step (a), a first enzyme-mediated luminescence reaction mediated by a first *Photinus pyralis* luciferase or a functional equivalent thereof is initiated; and
in step (c), a second enzyme-mediated luminescence reaction mediated by a second *Renilla reniformis* luciferase or a functional equivalent thereof is initiated.

40. The method according to claim 39, wherein in step (c), the first *Photinus pyralis* luciferase-mediated reaction is quenched, and the second *Renilla reniformis* luciferase-mediated reaction is initiated with a quench-and-activate composition comprising one or more quench reagents selected from the group consisting of
iodide,
iodine,
sulfate,
nitrate,
iso-propanol,
2-(4-aminophenyl)-6-methylbenzothiazole,
dimethyldecylphosphine oxide,
pyrophosphate,
benzothiazole,
2-phenylbenzothiazole,
trans-1,2,-diaminocyclohexane-N,N,N',N'-tetraacetic acid,
2-(6'-hydroxy-2'-benzothiazolyl)-thiazole-4-carboxylic acid,
ethylenediaminetetraacetic acid,
2(o-hydroxyphenyl)benzothiazole,
India fountain pen ink,
adenosine 5'-triphosphate 2',3'-acyclic dialcohol, periodate oxidized, borohydride reduced,
and mixtures thereof; and
an initiating reagent comprising initiating reagents selected from the group consisting of coelenterate luciferins, functional equivalents thereof, and mixtures thereof.

41. The method according to claim 39, wherein in step (c), the first *Photinus pyralis* luciferase-mediated reaction is quenched, and the second *Renilla reniformis* luciferase-mediated reaction is initiated with a quench-and-activate composition comprising mixtures selected from the group consisting of
Na$_4$PPi, and coelenterazine;
Na$_4$PPi, NaI, and coelenterazine;
Na$_4$PPi, CDTA, and coelenterazine;
Na$_4$PPi, CDTA, APMBT, and coelenterazine;
Na$_4$PPi, APMBT, Na$_2$SO$_4$, and coelenterazine;
Na$_4$PPi, CDTA, APMBT, Na$_2$SO$_4$, and coelenterazine;
Na$_4$PPi, APMBT, and coelenterazine;
APMBT, CDTA, and coelenterazine;
and mixtures thereof.

42. The method according to claim 41, wherein in step (c), the first *Photinus pyralis* luciferase-mediated reaction is quenched, and the second *Renilla reniformis* luciferase-mediated reaction is initiated with a quench-and-activate composition comprising a mixture selected from the group consisting of Na$_4$PPi, APMBT, Na$_2$SO$_4$, and coelenterazine; and Na$_4$PPi, CDTA, APMBT, Na$_2$SO$_4$, and coelenterazine.

43. The method according to claim 26, wherein in step (a), a first enzyme-mediated luminescence reaction mediated by a first *Pyrophorus plagiophthalamus* luciferase is initiated; and in step (c), a second enzyme-mediated luminescence reaction mediated by a second *Renilla reniformis* luciferase is initiated.

44. The method according to claim 26, wherein in step (a), a first enzyme-mediated luminescence reaction mediated by a first *Renilla reniformis* luciferase is initiated; and in step (c), a second enzyme-mediated luminescence reaction mediated by a second *Photinus pyralis* luciferase is initiated.

45. The method according to claim 26, further comprising the following step:

(e) subsequent to quantifying luminescence energy produced by the second enzyme-mediated luminescence reaction, quenching the second enzyme-mediated luminescence reaction by introducing at least one second quench reagent to the second enzyme-mediated luminescence reaction, wherein said at least one second quench reagent is capable of reducing photon emissions from the second enzyme-mediated luminescence reaction by a factor of at least 1,000-fold.

46. A method of assaying enzyme-mediated luminescence reactions within multisample assay plates comprising:

(a) initiating at least one enzyme-mediated luminescence reaction;

(b) quantifying luminescence energy produced by the luminescence reaction; and (c) quenching the enzyme-mediated luminescence reaction by introducing at least one quench reagent to the luminescence reaction;

whereby refractive interference of light between samples within the multisample assay plate is eliminated.

47. The method according to claim 46, wherein in step (a), at least one luciferase-mediated luminescence reaction is initiated.

48. An enzyme-mediated luminescence reaction assay kit comprising:

at least one quench reagent composition capable of quenching photon emission from an enzyme-mediated luminescence reaction by a factor of at least 1,000-fold;

a suitable first container, said at least one quench reagent composition disposed therein;

at least one functional enzyme substrate corresponding to the enzyme-mediated luminescence reaction being assayed;

a suitable second container, said at least one functional enzyme substrate disposed therein; and instructions for use.

49. The kit according to claim 48, wherein said at least one functional enzyme substrate corresponding to the enzyme-mediated luminescence reaction being assayed is a functional luciferase substrate.

50. The kit according to claim 49, wherein said at least one quench reagent composition comprises quench reagents selected from the group consisting of iodide,
iodine,
sulfate,
nitrate,
iso-propanol,
2-(4-aminophenyl)-6-methylbenzothiazole,
dimethyldecylphosphine oxide,
pyrophosphate,
benzothiazole,
2-phenylbenzothiazole,
n-butanol,
trans- 1,2,-diaminocyclohexane-N,N,N',N'-tetraacetic acid,
2-(6'-hydroxy-2'-benzothiazolyl)-thiazole-4-carboxylic acid,
ethylenediaminetetraacetic acid,
2(o-hydroxyphenyl)benzothiazole,
India fountain pen ink
adenosine 5'-triphosphate 2',3'-acyclic dialcohol, periodate oxidized, borohydride reduced,
sodium dodecyl sulfate,
citric acid,
Tween®20,
Triton®X-100,
and mixtures thereof.

51. The kit according to claim 50, wherein said at least one quench reagent composition is at least one mixture selected from the group consisting of $Na_4PPi$ and NaI;
$Na_4PPi$, CDTA, and APMBT;
$Na_4PPi$, APMBT, and $Na_2SO_4$;
$Na_4PPi$, CDTA, APMBT, and $Na_2SO_4$;
$Na_4PPi$ and APMBT;
$Na_4PPi$ and iso-propanol;
APMBT and CDTA;
NaI and $I_2$;
SDS and NaI;
Tween®20 and NaI;
Tween®20, NaI, and n-butanol;
Triton®X-100 and NaI;
and mixtures thereof.

52. A dual-reporter enzyme-mediated luminescence reaction assay kit comprising:

a first functional enzyme substrate corresponding to a first enzyme-mediated luminescence reaction being assayed;

a suitable first container, said first functional enzyme substrate disposed therein;

a quench-and-activate composition comprising quench reagents capable of quenching photon emission from the first enzyme-mediated luminescence reaction by a factor of at least 1,000-fold, and a second and distinct functional enzyme substrate corresponding to a second and distinct enzyme-mediated luminescence reaction;

a suitable: second container, said quench-and-activate composition disposed therein; and instructions for use.

53. The kit according to claim 52, wherein said first functional enzyme substrate, and said second and distinct functional enzyme substrate are luciferase substrates.

54. The kit according to claim 53, wherein said quench-and-activate composition comprises one or more quench reagents selected from the group consisting of iodide,
iodine,
sulfate,
nitrate,
iso-propanol,
(4-aminophenyl)-6-methylbenzothiazole,
dimethyldecylphosphine oxide,
pyrophosphate,
n-butanol,
benzothiazole,
2-phenylbenzothiazole, trans-1,2,-diaminocyclohexane-N,N,N',N'-tetraacetic acid,
2-(6'-hydroxy-2'-benzothiazolyl)-thiazole-4-carboxylic acid,
ethylenediaminetetraacetic acid,
2(o-hydroxyphenyl)benzothiazole,
India fountain pen ink,
adenosine 5'-triphosphate 2',3'-acyclic dialcohol,
periodate oxidized,
borohydride reduced,
sodium dodecyl sulfate,
citric acid,
Tween®20,
Triton®X-100,
and mixtures thereof; and
a second and distinct functional luciferase substrate selected from the group consisting of coelenterate luciferins and functional equivalents thereof, beetle luciferins and functional equivalents thereof, and mixtures thereof.

55. The kit according to claim 54, wherein said quench-and-activate composition comprises mixtures selected from the group consisting of
$Na_4PPi$, and coelenterazine;
$Na_4PPi$, NaI, and coelenterazine;
$Na_4PPi$, CDTA, and coelenterazine;
$Na_4PPi$, CDTA, APMBT, and coelenterazine;
$Na_4PPi$, APMBT, $Na_2SO_4$, and coelenterazine;
$Na_4PPi$, CDTA, APMBT, $Na_2SO_4$, and coelenterazine;
$Na_4PPi$, APMBT, and coelenterazine;
APMBT, CDTA, and coelenterazine;
and mixtures thereof.

56. The kit according to claim 52, further comprising:
a second quench reagent capable of quenching photon emission from the second and distinct enzyme-mediated reaction, and
a suitable third container, said second quench reagent disposed therein.

57. Enzyme-mediated luminescence reaction quench reagents capable of reducing photon emissions from enzyme-mediated luminescence reactions comprising:
iodide,
iodine,
sulfate,
nitrate,
iso-propanol,
2-(4-aminophenyl)-6-methylbenzothiazole,
dimethyldecylphosphine oxide,
pyrophosphate,
benzothiazole,
2-phenylbenzothiazole,
n-butanol,
trans-1,2,-diaminocyclohexane-N,N,N',N'-tetraacetic acid,
2-(6'-hydroxy-2'-benzothiazolyl)-thiazole-4-carboxylic acid,
ethylenediaminetetraacetic acid,
2(o-hydroxyphenyl)benzothiazole,
India fountain pen ink,
adenosine 5'-triphosphate 2',3'-acyclic dialcohol, periodate oxidized, borohydride reduced
sodium dodecyl sulfate,
citric acid,
Tween®20,
Triton®X-100,
and mixtures thereof.

58. Enzyme-mediated luminescence reaction quench reagents according to claim 57, comprising:
mixtures selected from the group consisting of
SDS and NaI;
$I_2$ and NaI;
$Na_4PPi$ and NaI;
$Na_4PPi$, CDTA, and APMBT;
$Na_4PPi$, APMBT, and $Na_2SO_4$;
$Na_4PPi$, CDTA, APMBT, and $Na_2SO_4$;
$Na_4PPi$ and APMBT;
$Na_4PPi$ and iso-propanol;
IFP Ink and APMBT;
APMBT and CDTA;
IFP Ink and CDTA;
IFP Ink and $Na_4PPi$;
SDS and NaI;
Tween®20 and NaI;
Tween®20, NaI, and n-butanol;
Triton®X-100 and NaI;
and mixtures thereof;
contained within assay-suitable solvents.

59. Enzyme-mediated luminescence reaction quench reagents according to claim 58, selected from the group consisting of SDS and NaI; $Na_4PPi$ and NaI; and $Na_4PPi$, CDTA, APMBT, and $Na_2SO_4$.

60. Enzyme-mediated luminescence reaction quench-and-activate reagents according to claim 58, selected from the group consisting of $Na_4PPi$, APMBT, $Na_2SO_4$, and coelenterazine; and $Na_4PPi$, CDTA, APMBT, $Na_2SO_4$, and coelenterazine.

* * * * *

UNITED STATES PATENT AND TRADEMARK OFFICE
CERTIFICATE OF CORRECTION

PATENT NO.     : 5,744,320
DATED          : April 28, 1998
INVENTOR(S)    : Bruce A. Sherf, Keith V. Wood and Elaine T. Schenborn It is certified that error appears in the above-identified patent and that said Letters Patent is hereby corrected as shown below:

Column 1,
Line 11, "one:" should be -- one --.
Line 30, "reportel" should be -- reporter --.
Line 35, "dioxctanes" should be -- dioxetanes --.
Line 53, "iuminescence" should be -- luminescence --.

Column 2,
Line 15, "microtiler" should be -- microtiter --.
Line 38, "Demnark" should be -- Denmark --.

Column 3
Line 12, "manufacture" should be -- manufacturer --.
Line 66, after "of" delete "a".

Column 4,
Line 41, "perfomance" should be -- performance --.

Column 5,
Line 3, "commonaillies" should be -- commonalities --.
Line 36, "this" should be -- thus --.
Line 65, "100.000" should be -- 100,000 --.

Column 6,
Line 8, "microliter" should be -- microtiter --.
Line 11, "sample.," should be -- sample, --.
Line 65, "luciferase,-mediated" should be -- luciferase-mediated --.

Column 8,
Delete lines 28-32, and insert -- FIG. 3 is a graph showing the elimination of signal cross-talk by the use of the present invention. --.
Delete lines 33-36, and insert -- FIG. 4 is a graphic representation of the data presented in the two right-hand columns of Table 2, *infra*. --.

Column 9,
Line 17, in the table entry for HPBT, the chemical name "2(O-Hydroxyphenyl) benzothiazole" should be -- 2-(o-Hydroxyphenyl)benzothiazole --.
Line 18, in the table entry for HEPES, "ethansulfonic" should be -- ethanesulfonic --.
Lines 45 - 48, the chemical terms "2-(6'-hydroxy-2'-benzothiazolyl)-thiazole-4carboxylic acid, ethylenediaminetetrethylenediaminetetraacetic acid, 2-(o-hydroxyphenyl) benzothiazole," should be -- 2-(6'-hydroxy-2'-benzothiazolyl)-thiazole-4-carboxylic acid, ethylenediaminetetraacetic acid, 2-(o-hydroxyphenyl)benzothiazole, --.
Line 55, "$I_2$ and I" should be -- $I_2$ and NaI --.

UNITED STATES PATENT AND TRADEMARK OFFICE
CERTIFICATE OF CORRECTION

PATENT NO.    : 5,744,320
DATED         : April 28, 1998
INVENTOR(S)   : Bruce A. Sherf, Keith V. Wood and Elaine T. Schenborn It is certified that error appears in the above-identified patent and that said Letters Patent is hereby corrected as shown below:

Column 10,
Line 9, "luciterases" should be -- luciferases --.
Line 62, "reactions." should be -- reactions --.
Lines 63-65, should be in bold typeface to denote a heading.

Column 11
Line 1, "Luciferuse" should be -- Luciferase --.
Line 10, "luciferuse" should be -- luciferase --.
Line 33, "Reagent" should be -- Reagent (LAR) --.
Line 33, "6D" should be -- 1A --.
Line 40, "6D" should be -- 1A --.

Column 12,
Line 34, "lumincence" should be -- luminescence --.
Line 41, "the:" should be -- the --.

Column 13,
Line 55, "3-B" should be -- 3 --.
Line 62, "3-B" should be -- 3 --; and "3-A" should be -- 2 --.

Column 14,
Line 43, "3-A" should be -- 2 --.
Line 47, "3-B" should be -- 3 --.
Line 50, insert the heading -- Table 2 --.

Column 15,
Lines 3 and 4, should be in bold to denote a heading.
Table 3, left-hand column, first entry, "inhibitior" should be -- Inhibitor --.

Column 16,
Line 24, "FIG. 4 demonstrates" should be -- FIGS. 5 and 6 demonstrate --.
Line 34, "Y-axis of FIG 4 is" should be -- Y axes of FIGS. 5 and 6 are --.

Column 17,
Line 10, "FIG. 4 also demonstrates" should be -- FIGS. 5 and 6 also demonstrate --.
Lines 27 and 28, "FIG. 4" should be -- FIGS. 5 and 6 --.
Lines 31 and 32, should be in bold typeface to denote a heading.
Line 40, "luminesces" should be -- luminescence --.
Line 62, "NaCl mM" should be -- NaCl, 1 mM --.

UNITED STATES PATENT AND TRADEMARK OFFICE
CERTIFICATE OF CORRECTION

PATENT NO.    : 5,744,320
DATED         : April 28, 1998
INVENTOR(S)   : Bruce A. Sherf, Keith V. Wood and Elaine T. Schenborn It is certified that error appears in the above-identified patent and that said Letters Patent is hereby corrected as shown below:

Column 18
Line 24, should be in bold typeface to denote a heading.

Column 19,
Line 5, "film" should be -- from --.

Column 20
Line 13, "frown" should be -- from --.
Line 17, after the word "Renilla" insert -- luciferase --.

Column 21,
Line 20, "iuminescence" should be -- luminescence --.
Line 21, "luciterase" should be -- luciferase --.
Line 59, should be in bold typeface to denote a heading.

Column 22,
Line 17, ":rapidly" should be -- rapidly --.
Line 46, "3-A" should be -- 2 --.

Column 23,
Line 1, "3-B" should be -- 3 --.
Line 3, "3-A" should be -- 2 --.
Line 9, "3-B" should be -- 3 --.
Line 23, "3-A" should be -- 2 --.
Line 25, "3-B" should be -- 3 --.
Line 45, delete "FIG. 4" and insert -- Tables 1 and 3 each --.
Line 47, delete "three".
Line 48, after the word "Formulations" insert -- of --.

Column 25,
Line 10, "2(o-hydroxyphenyl)benzothiazole" should be -- 2-(o-hydroxyphenyl) benzothiazole --.
Line 34, delete "SDS and NaI;".
Line 47, "lumincscence" should be -- luminescence --.

Column 27,
Line 2, "2(o-hydroxyphenyl)benzothiazole" should be -- 2-o-hydroxyphenyl) benzothiazole --.
Line 24, "Ink," should be -- Ink --.
Line 39, "*pyrophorus*" should be -- *Pyrophorus* --.
Line 57, "2(o-hydroxyphenyl)benzothiazole" should be -- 2-(o-hydroxyphenyl) benzothiazole --.

UNITED STATES PATENT AND TRADEMARK OFFICE
CERTIFICATE OF CORRECTION

PATENT NO.    : 5,744,320                                    Page 4 of 5
DATED         : April 28, 1998
INVENTOR(S)   : Bruce A. Sherf, Keith V. Wood and Elaine T. Schenborn It is certified that error appears in the above-identified patent and that said Letters Patent is hereby corrected as shown below:

Column 27 (cont'd),
Line 64, "*pyrophorus*" should be -- *Pyrophorus* --.

Column 28,
Line 7, "C.DTA" should be -- CDTA --.
Line 10, "Ink," should be -- Ink --.
Line 13, immediately prior to the word "Ink" insert -- IFP --.
Line 34, "Tween®b 20" should be -- Tween® 20 --.
Line 47, "NaI" should be -- NaI; --.

Column 29,
Line 15, "1,000-fold." should be -- 1,000-fold is introduced. --.
Line 43, "2(o-hydroxyphenyl)benzothiazole" should be -- 2-(o-hydroxyphenyl)benzothiazole --.

Column 30,
Line 34, "trans-1,2,-diaminocyclohexane-N,N,N',N'-tetraacetic acid," should be -- trans-1,2-diaminocyclohexane-N,N,N',N'-tetraacetic acid, --.
Line 38, "2(o-hydroxyphenyl)benzothiazole" should be -- 2-(o-hydroxyphenyl)benzothiazole --.
Line 52, "$Na_4PPi$," should be -- $Na_4PPi$ --.

Column 32,
Line 9, "2(o-hydroxyphenyl)benzothiazole" should be -- 2-(o-hydroxyphenyl)benzothiazole --.
Line 10, "Ink" should be -- Ink, --.
Line 48, "suitable:" should be -- suitable --.

Column 33,
Line 1, "trans-1,2,-diaminocyclohexane-N,N,N',N'-tetraacetic acid," should be -- trans-1,2-diaminocyclohexane-N,N,N',N'-tetraacetic acid, --.
Line 5 (claim 54), "2(o-hydroxyphenyl)benzothiazole" should be -- 2-(o-hydroxyphenyl)benzothiazole --.
Lines 7, 8 and 9, the three chemical terms
"adenosine 5'-triphosphate 2',3'-acyclic dialcohol,"
"periodate oxidized,"
"borohydride reduced," should read as the single chemical name
-- adenine 5'-triphosphate 2',3' acyclic dialcohol, periodate oxidized, borohydride reduced, --.
Line 22, "$Na_4PPi$," should be -- $Na_4PPi$ --.

UNITED STATES PATENT AND TRADEMARK OFFICE
CERTIFICATE OF CORRECTION

PATENT NO. : 5,744,320
DATED : April 28, 1998
INVENTOR(S) : Bruce A. Sherf, Keith V. Wood and Elaine T. Schenborn It is certified that error appears in the above-identified patent and that said Letters Patent is hereby corrected as shown below:

<u>Column 34,</u>
Line 4, "trans-1,2,-diaminocyclohexane-N,N,N',N'-tetraacetic acid," should be
-- trans-1,2-diaminocyclohexane-N,N,N',N'-tetraacetic acid, --.
Line 8, "2(o-hydroxyphenyl)benzothiazole" should be -- 2-(o-hydroxyphenyl) benzothiazole --.
Line 11, "reduced" should be -- reduced, --.
Line 43, delete "according to claim 58," and insert -- in a kit according to claim 55 and --.

Signed and Sealed this

Eighth Day of November, 2005

JON W. DUDAS
*Director of the United States Patent and Trademark Office*